United States Patent
Fukuda et al.

(10) Patent No.: US 10,363,018 B2
(45) Date of Patent: Jul. 30, 2019

(54) MEDICAL PROCESSING APPARATUS AND MEDICAL PROCESSING METHOD

(71) Applicant: Toshiba Medical Systems Corporation, Otawara-shi (JP)

(72) Inventors: Shogo Fukuda, Kawasaki (JP); Yasuhiko Abe, Otawara (JP); Tetsuya Kawagishi, Kawasaki (JP); Koji Ando, Otawara (JP); Mitsuo Akiyama, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 62 days.

(21) Appl. No.: 15/652,463

(22) Filed: Jul. 18, 2017

(65) Prior Publication Data

US 2018/0021024 A1    Jan. 25, 2018

(30) Foreign Application Priority Data

Jul. 19, 2016   (JP) .................. 2016-141398
Jun. 23, 2017   (JP) .................. 2017-122988

(51) Int. Cl.
*A61B 8/00*       (2006.01)
*G06T 11/60*      (2006.01)
*G06T 7/00*       (2017.01)
*A61B 8/08*       (2006.01)
*G06T 7/11*       (2017.01)
(Continued)

(52) U.S. Cl.
CPC .......... *A61B 8/5215* (2013.01); *A61B 8/0883* (2013.01); *A61B 8/14* (2013.01); *A61B 8/463* (2013.01); *A61B 8/5223* (2013.01); *G06T 7/0012* (2013.01); *G06T 7/11* (2017.01); *G06T 11/206* (2013.01); *G06T 11/60* (2013.01); *G06T 2207/10081* (2013.01); *G06T 2207/10088* (2013.01); *G06T 2207/10132* (2013.01); *G06T 2207/30048* (2013.01)

(58) Field of Classification Search
CPC .......... G06T 11/206; G06T 11/60; G06T 7/11; G06T 7/0012; G06T 2207/10081; A61B 8/5215; A61B 8/5223; A61B 8/463; A61B 8/14; A61B 8/0883
See application file for complete search history.

(56) References Cited

U.S. PATENT DOCUMENTS 6,674,879 B1 * 1/2004 Weisman ............... A61B 8/06
                                              378/94
2009/0112088 A1  4/2009 Ohuchi et al.
(Continued)

FOREIGN PATENT DOCUMENTS

JP  2009-106548   5/2009
JP  2012-055483   3/2012
JP  2014-171556   9/2014

*Primary Examiner* — Jon Chang
(74) *Attorney, Agent, or Firm* — Oblon, McClelland, Maier & Neustadt, L.L.P.

(57) ABSTRACT

According to one embodiment, a medical processing apparatus includes processing circuitry. The processing circuitry adds incidental information including information regarding a kind concerning each of a plurality of regions in a heart to an analysis result of each of the regions. The analysis result is obtained by analyzing medical data. The processing circuitry determines a display position of the analysis result of each of the regions based on the incidental information.

21 Claims, 19 Drawing Sheets

(51) Int. Cl.
*A61B 8/14* (2006.01)
*G06T 11/20* (2006.01)

(56) References Cited

U.S. PATENT DOCUMENTS

2012/0165674 A1 6/2012 Abe et al.
2015/0342571 A1 12/2015 Ohuchi et al.

\* cited by examiner

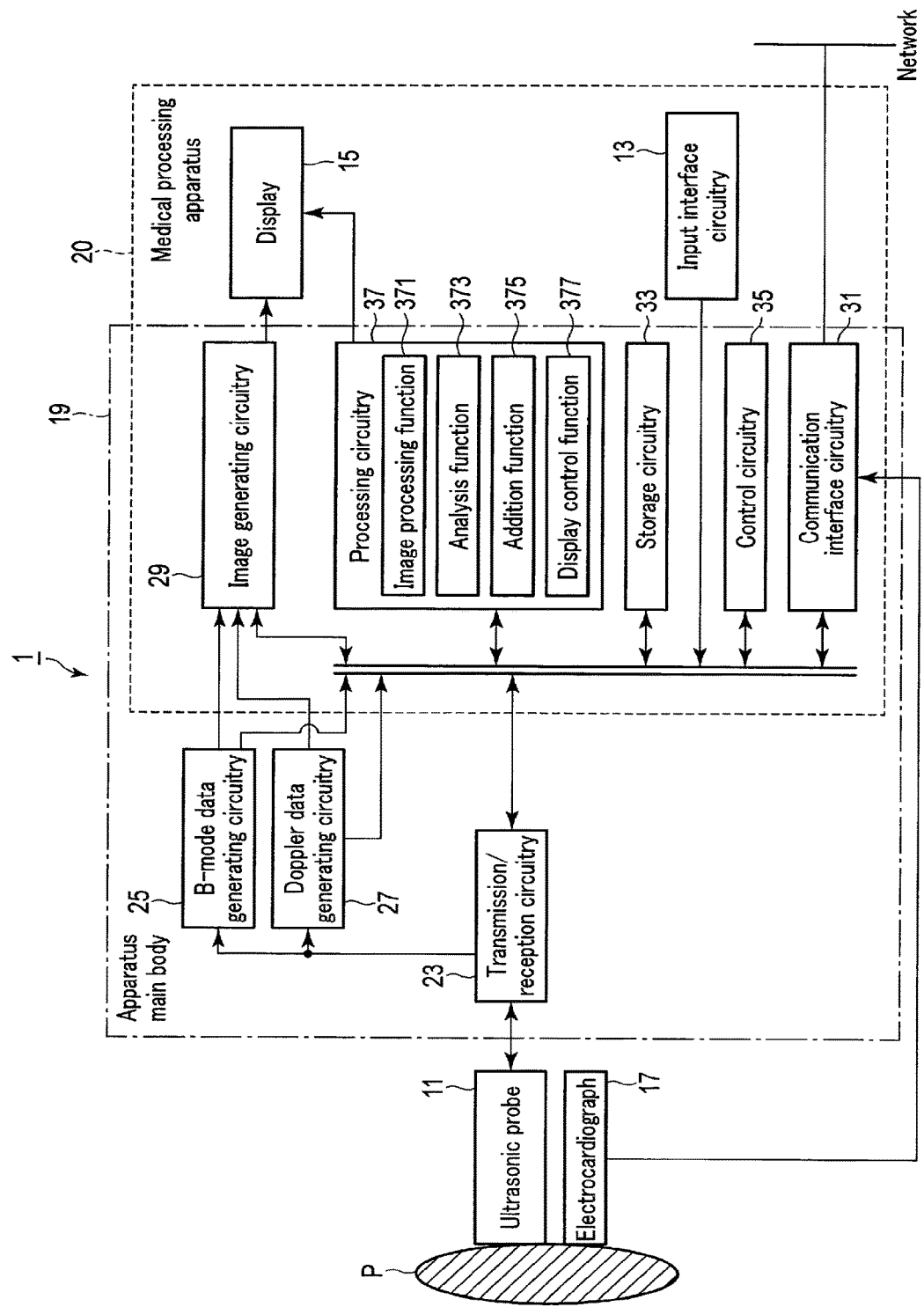
F I G. 1

(a)

| Patient ID | Kind of heart chamber | Collection date and time | Phase of stress echo | Progress of treatment | Image mode | Analysis parameter name | ... |
|---|---|---|---|---|---|---|---|
| 1234 | Left ventricle | 2015/1/10 | No stress | Before CRT treatment | Short-axis tomographic images (Apical) | Longitudinal strain | ... |

(b)

| Patient ID | Kind of heart chamber | Collection date and time | Phase of stress echo | Progress of treatment | Image mode | Analysis parameter name | ... |
|---|---|---|---|---|---|---|---|
| 0123 | Left ventricle | 2016/1/10 | No stress | Before CRT treatment | Polar map | Radial strain | ... |

(c)

| Patient ID | Kind of heart chamber | Collection date and time | Phase of stress echo | Progress of treatment | Image mode | Analysis parameter name | ... |
|---|---|---|---|---|---|---|---|
| 2345 | Left atrium | 2015/2/10 | No stress | Before CRT treatment | Surface rendering | Peek arrival time | ... |

F I G. 3

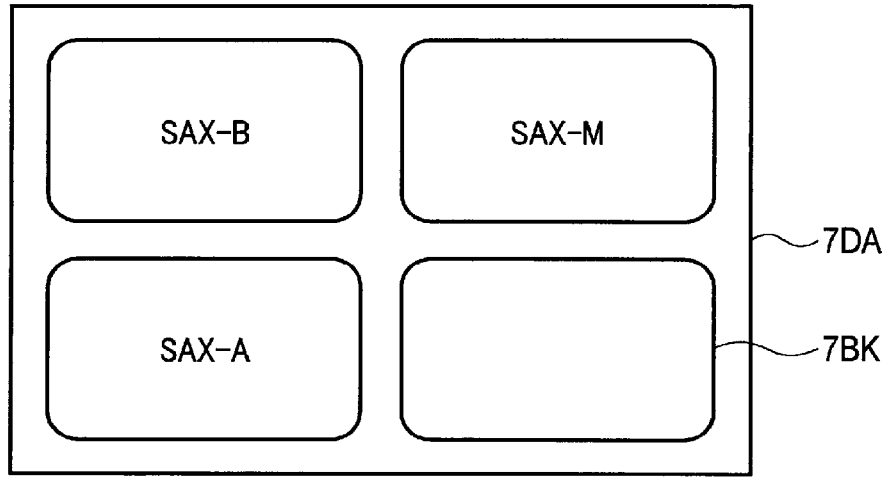
F I G. 7
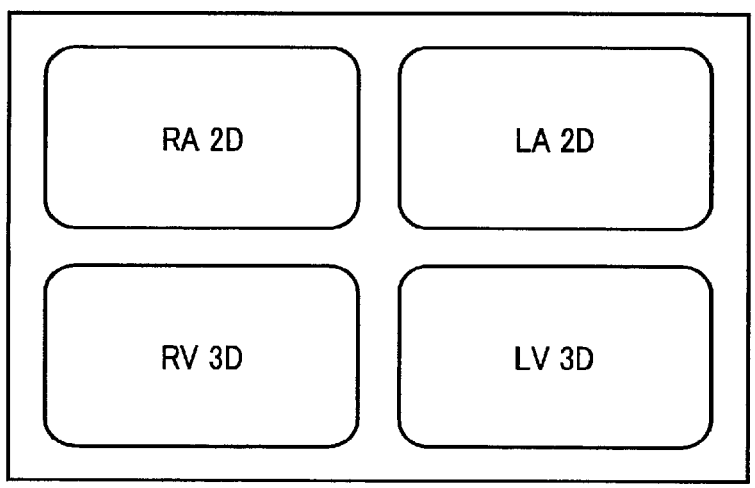
F I G. 8

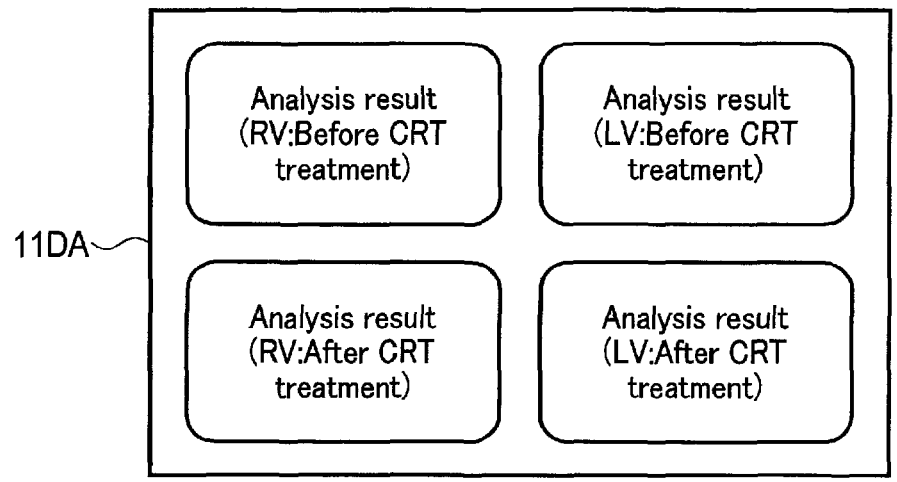
F I G. 11
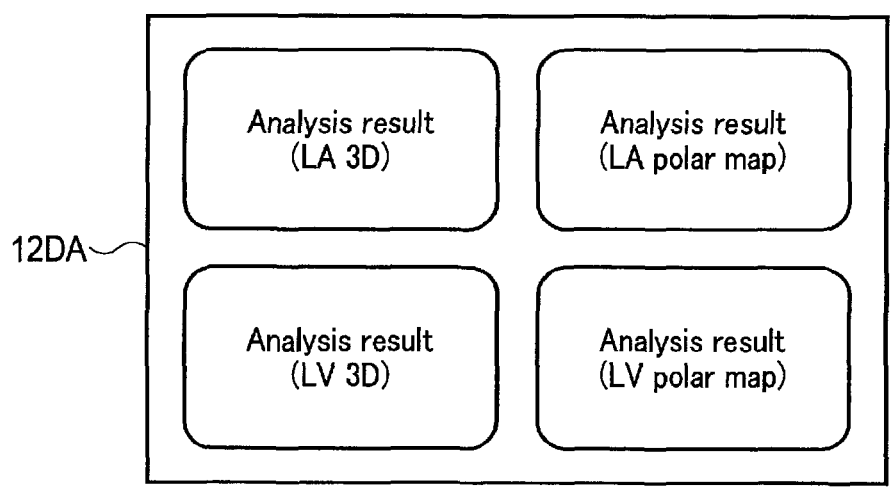
F I G. 12

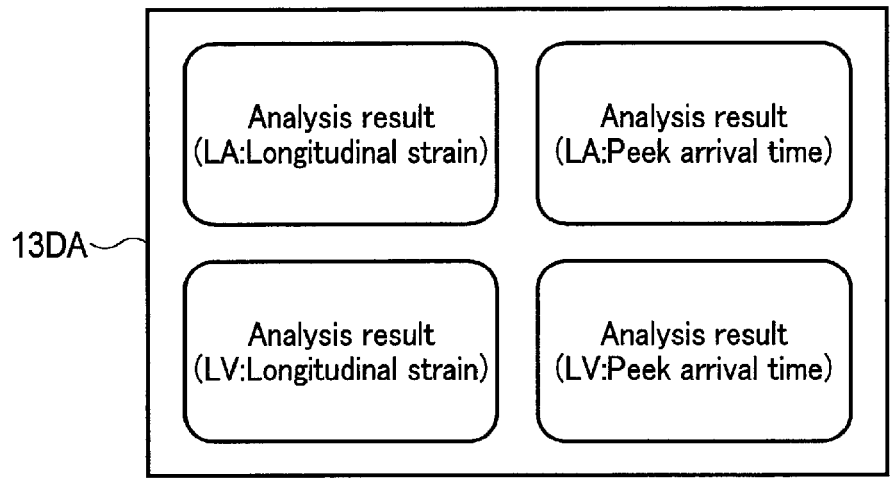
F I G. 13
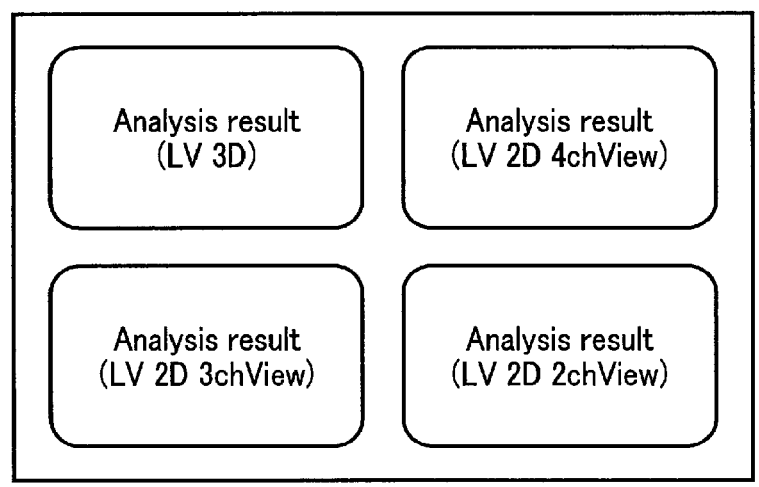
F I G. 14

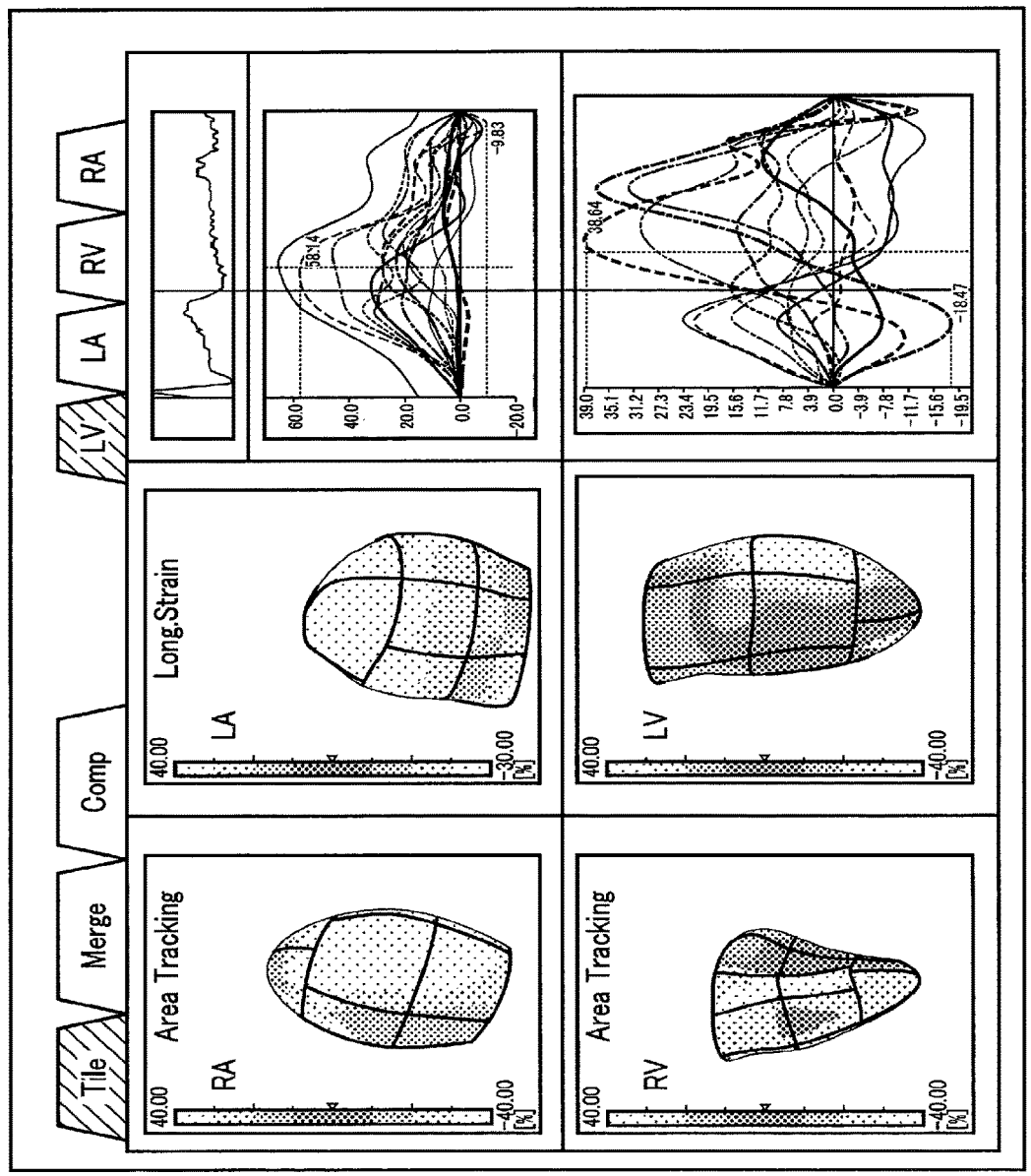
F I G. 16

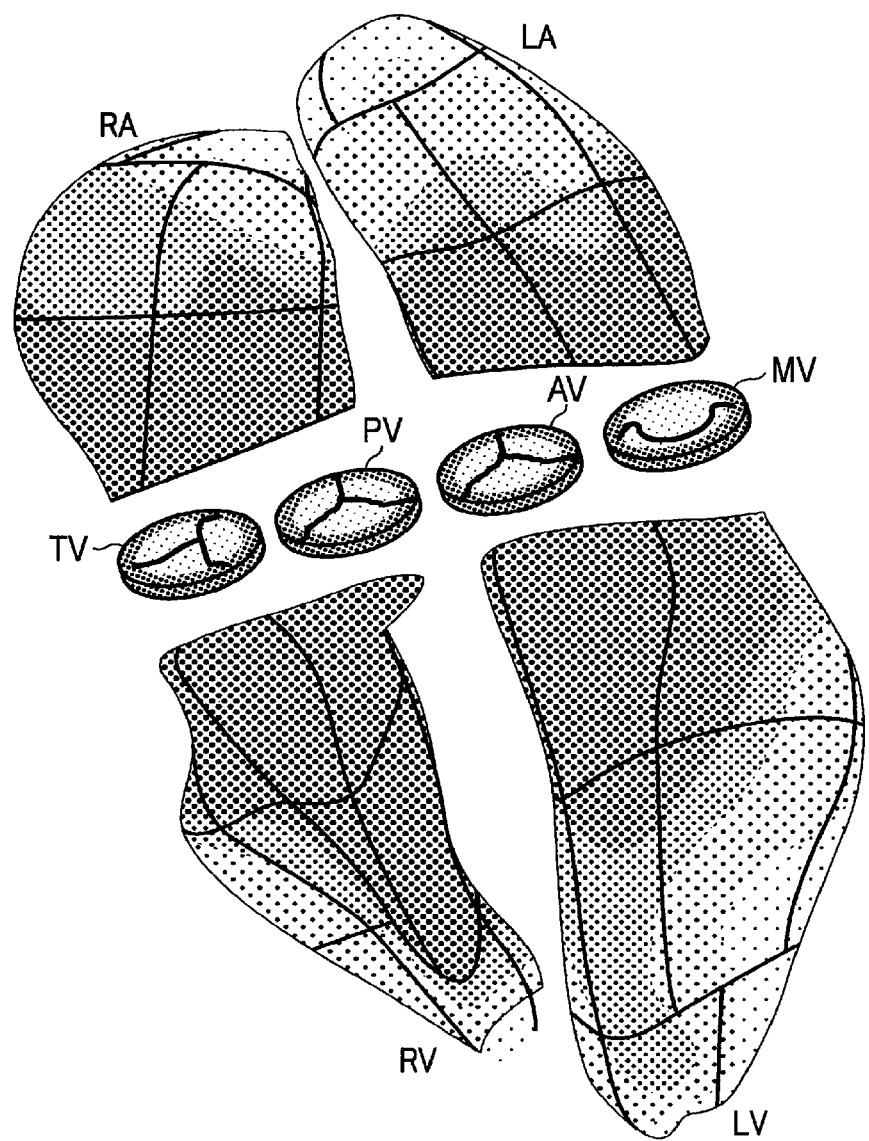
F I G. 20

MEDICAL PROCESSING APPARATUS AND MEDICAL PROCESSING METHOD

CROSS-REFERENCE TO RELATED APPLICATIONS

This application is based upon and claims the benefit of priority from the prior Japanese Patent Application No. 2016-141398, filed Jul. 19, 2016, and No. 2017-122988, filed Jun. 23, 2017, the entire contents of all of which are incorporated herein by reference.

FIELD

Embodiments described herein rerate generally to a medical processing apparatus and a medical processing method.

BACKGROUND

A conventional ultrasound diagnostic apparatus had a function for analyzing a local wall motion regarding a single heart chamber, and displaying an analysis result. The conventional ultrasound diagnostic apparatus did not have a function for analyzing local wall motions regarding a plurality of heart chambers, and uniformly displaying these analysis results.

The object is to provide a medical processing apparatus and a medical processing method that are capable of displaying the analysis results regarding a plurality of regions in a heart in a desired layout by a simplified operation.

BRIEF DESCRIPTION OF THE DRAWINGS

FIG. 1 is a schematic view showing a configuration of an ultrasound diagnostic apparatus according to an embodiment.

FIG. 3 shows an example of incidental information in the present embodiment.

FIG. 7 shows an example of a layout of analysis results regarding comparison of short-axis tomographic images in the present embodiment.

FIG. 8 shows an example of a layout of analysis results in which three-dimensional images and two-dimensional images are mixed in the present embodiment.

FIG. 11 shows an example of a layout of analysis results regarding a comparison of two chambers before and after treatment in the present embodiment.

FIG. 12 shows an example of a layout of analysis results regarding a comparison of two chambers with different image modes in the present embodiment.

FIG. 13 shows an example of a layout of analysis results regarding a comparison of two chambers with different analysis parameters in the present embodiment.

FIG. 14 shows an example of a layout of analysis results of different image modes in the present embodiment.

FIG. 16 shows a display example of displaying analysis results of four chambers together with a plurality of tabs in a second modification of the present embodiment.

FIG. 20 shows an example of a composite image obtained by combining the analysis results of four chambers and four valves in the fourth modification of the present embodiment.

DETAILED DESCRIPTION

Figure 2:
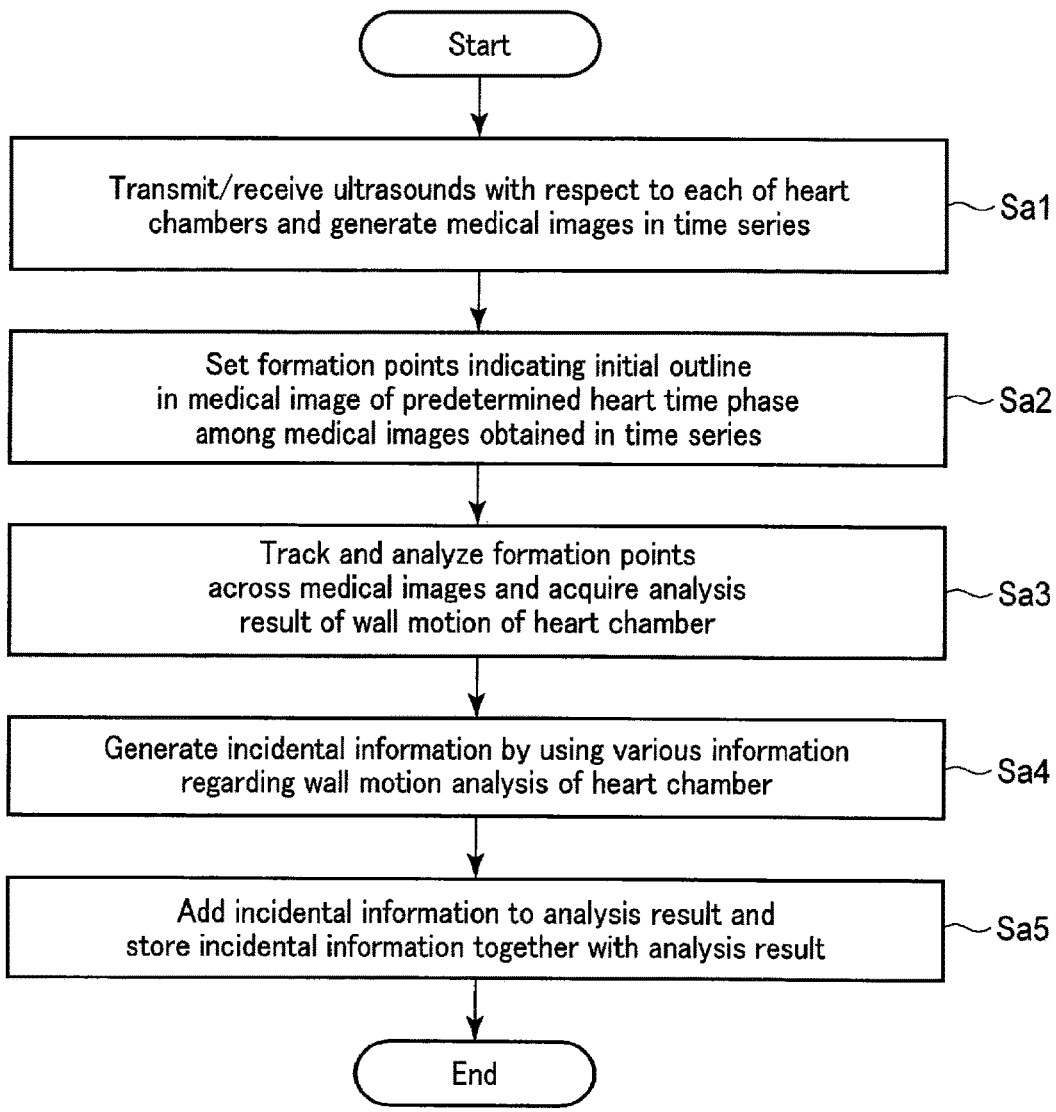
FIG. 2 is a flowchart showing an example of a processing procedure regarding an addition function in the present embodiment.

In general, according to one embodiment, a medical processing apparatus according to the present embodiment includes processing circuitry. The processing circuitry adds incidental information including information regarding a kind concerning each of a plurality of regions in a heart to an analysis result of each of the regions. The analysis result is obtained by analyzing medical data. The processing circuitry determines a display position of the analysis result of each of the regions based on the incidental information.

An ultrasound diagnostic apparatus according to the present embodiment will be explained with reference to the accompanying drawings. In the description below, structural elements having substantially the same configurations will be denoted by the same reference symbols, and a repetitive description of such elements will be given only where necessary.

FIG. 1 is a schematic view showing a configuration of an ultrasound diagnostic apparatus 1 according to the present embodiment. As shown in FIG. 1, the ultrasound diagnostic apparatus 1 includes an ultrasonic probe 11, an input interface circuitry (input unit) 13, a display (display unit) 15, an electrocardiograph 17, and an apparatus main body 19.

The ultrasonic probe 11 comprises a plurality of piezoelectric transducers, a matching layer provided on an ultrasonic wave radiation surface side of the piezoelectric transducer, and a backing material provided on a back surface side of the piezoelectric transducer, etc. Each of the plurality of piezoelectric transducers generates ultrasound in response to a drive signal supplied from transmission/reception circuitry 23 explained later on. The ultrasonic probe 11 is, for example, a two-dimensional array probe in which a plurality of piezoelectric transducers are arrayed along an azimuth direction and an elevation direction that are orthogonal to each other. The two-dimensional array probe is, for example, a two-dimensional sector probe. The ultrasonic probe 11 is not limited to the two-dimensional array probe which is capable of performing three-dimensional scanning, and may also be a mechanical four-dimensional probe. In the case where the ultrasonic probe 11 is a one-dimensional array probe that is capable of performing two-dimensional scanning, a three-dimensional echo signal may be obtained by an operation of an operator swinging the ultrasonic probe 11 in an elevation direction.

The input interface circuitry 13 loads various types of instructions, commands, information, options, and settings from an operator into the present ultrasound diagnostic apparatus 1. The input interface circuitry 13 is realized by a trackball, a switch button, a mouse, a keyboard, a touch pad through which an input operation is carried out by touching an operation surface, and a touch panel display with an integrated display screen and touch pad, etc. The input interface circuitry 13 converts the input operation received from the operator into an electric signal. In the present specification, the input interface circuit 13 is not limited to physical operation members such as a mouse and a keyboard. The input interface circuitry 13 also includes, for example, electric signal processing circuitry that receives an electric signal corresponding to an input operation from an external input device provided separately from the present ultrasound diagnostic apparatus 1, and outputs the received electric signal to the apparatus main body 19.

The display 15 displays various images generated by image generating circuitry 29, etc. explained later on. The display 15 includes display circuitry that realizes display of various images. The display 15 displays a Graphics User Interface (GUI) for the operator to input various setting requirements. A plurality of displays may be connected to the apparatus main body 19 of the present ultrasound diagnostic apparatus 1.

The electrocardiograph 17 is connected to the apparatus main body 19 through communication interface circuitry 31. The electrocardiograph 17 acquires an electrocardiogram (ECG) of a subject P as a biological signal of the subject P that is subjected to ultrasonic scanning. The electrocardiograph 17 outputs the acquired electrocardiogram to the apparatus main body 19.

The apparatus main body 19 includes transmission/reception circuitry (transmission/reception unit) 23, B-mode data generating circuitry (B-mode data generating unit) 25, Doppler data generating circuitry (Doppler data generating unit) 27, image generating circuitry (image generating unit) 29, communication interface circuitry 31, storage circuitry (storage unit) 33, control circuitry (controller) 35, and processing circuitry (processing unit) 37.

The transmission/reception circuitry 23 includes a pulse generator, transmission delay circuitry, and pulser circuitry, and supplies a drive signal to each of a plurality of piezoelectric transducers in the ultrasonic probe 11. The pulse generator repeatedly generates rate pulses for forming transmission ultrasonic waves at a predetermined rate frequency $f_r$ Hz (cycle of period; $1/f_r$ second). The transmission delay circuitry gives each rate pulse a delay time necessary to focus transmission ultrasonic waves into a beam and determine transmission directivity. The pulser circuitry applies a voltage pulse to each of the piezoelectric transducers of the ultrasonic probe 11, as a drive signal, at a timing based on the rate pulse. According to this constitution, an ultrasonic beam is transmitted to the subject P.

The transmission/reception circuitry 23 further includes a preamplifier, an analog to digital (hereinafter, referred to as A/D) converter, reception delay circuitry, and an adder. The transmission/reception circuitry 23 generates a reception signal based on a received echo signal generated by each piezoelectric transducer. The preamplifier amplifies an echo signal from the subject P received via the ultrasonic probe 11 for each channel. The A/D converter converts the amplified received echo signal into a digital signal. The reception delay circuitry gives the received echo signal that has been converted into a digital signal a delay time necessary for determining reception directivity. The adder adds a plurality of echo signals to which the delay times are given. With this addition processing, the transmission/reception circuitry 23 generates a reception signal in which a reflection component from a direction corresponding to the reception directivity is enhanced. Comprehensive directivity of ultrasonic transmission/reception is determined by the transmission directivity and the reception directivity. An ultrasonic beam (so-called "ultrasonic scanning line") is determined by this comprehensive directivity.

In accordance with a scanning order set for each of a plurality of regions in a heart, the transmission/reception circuitry 23 may, for example, scan each of the regions by an ultrasonic wave. The regions are, for example, various heart chambers such as a left ventricle, a left atrium, a right ventricle, and a right atrium, and various valves such as a mitral valve (MV), an aortic valve (AV), a tricuspid value (TV), and a pulmonary valve (PV). Hereinafter, to simplify the explanation, the regions will be explained as heart chambers. The scanning order is, for example, performed in the order of the left ventricle, the left atrium, the right ventricle, and the right atrium, and corresponds to the regions. The scanning order is stored, for example, in the storage circuitry 33. The transmission/reception circuitry 23 generates a reception signal in a time series that corresponds to the regions.

The B-mode data generating circuitry 25 includes an envelope detector and a logarithmic converter, and generates B-mode data based on the reception signal. The envelope detector executes envelope detection of the reception signal. The logarithmic converter relatively emphasizes a weak signal in the envelope detected-signal by logarithmically converting the envelope-detected signal. The B-mode data generating circuitry 25 generates a signal value (referred to as B-mode data) for each depth on each scanning line based on the signal enhanced by the logarithmic converter. The B-mode data generating circuitry 25 generates volume data corresponding to three-dimensional B-mode data based on two-dimensional B-mode data obtained by two-dimensional scanning, or a reception signal obtained by three-dimensional scanning. For an easy-to-understand explanation, hereinafter, the volume data is assumed as being generated by performing three-dimensional ultrasonic scanning on each of the heart chambers in the subject P. Here, the generated volume data corresponds to each of the heart chambers. The heart chambers are at least two among four chambers. The four chambers are the left atrium (LA), the left ventricle (LV), the right atrium (RA), and the right ventricle (RV). The volume data may be generated by performing ultrasonic scanning with respect to the four chambers of the heart of the subject P.

The Doppler data generating circuitry 27 includes a mixer and a low pass filter (hereinafter referred to as an LPF) etc., and generates Doppler data based on the reception signal.

The mixer multiplies the reception signal by a reference signal having a frequency $f_0$ of a transmission ultrasonic wave to generate a signal having a component with a Doppler shift frequency $f_d$ and a signal having a frequency component of $(2f_0+f_d)$. The LPF removes a signal of a high-frequency component $(2f_0+f_d)$ from signals output from the mixer. In this way, the Doppler data generating circuitry 27 generates Doppler data having a component with a Doppler shift frequency $f_d$ from the reception signal.

The image generating circuitry 29 includes a digital scan converter (hereinafter referred to as DSC) and an image memory, etc. which are both not shown. The DSC converts a scanning line signal string for ultrasonic scanning, which is formed from the B-mode data and the Doppler data, into a scanning line signal string in a video format (scan conversion). The image generating circuitry 29 generates data of an ultrasonic image by combining character information of various parameters and a memory, etc. with respect to the scan-converted B-mode data and Doppler data. The data of the ultrasonic image is data for display. The ultrasonic image is an example of a medical image. The data of the ultrasonic image is an example of medical data. On the other hand, the B-mode data, the volume data, and the Doppler data are also referred to as raw data. The image memory stores a plurality of ultrasonic images corresponding to a series of frames of a freeze operation immediately before input. The ultrasonic images stored in the image memory are used for cine images.

The communication interface circuitry 31 is connected to an external device such as a medical image storage device through a network. The communication interface circuitry 31 receives the volume data, etc. of the subject P from the medical image storage device, and outputs it to the storage circuitry 33. The communication interface circuitry 31 transfers various data output from the image generating circuitry 29 and the processing circuitry 37 to the external device.

The storage circuitry 33 comprises various kinds of memory, an HDD (hard disk drive), an SSD (solid state drive), magnetic disks (such as Floppy (trademark) disks and hard disks), optical disks (such as CD-ROMs and DVDs), and semiconductor memories, etc. The storage circuitry 33 stores a program regarding ultrasonic transmission/reception, and a program corresponding to various processing executed by the control circuitry 35 and the processing circuitry 37, etc. The storage circuitry 33 stores raw data, ultrasonic image data, various data generated/processed by the processing circuitry 37, and scanning order, etc.

The control circuitry 35 includes, for example, a processor and a memory as a hardware resource. The control circuitry 35 functions as a center of the present ultrasound diagnostic apparatus 1. Specifically, the control circuitry 35 reads out a control program stored in the storage circuitry 33 and expands it in the memory to control various circuitry of the ultrasound diagnostic apparatus 1 in accordance with the expanded control program.

The processing circuitry 37 includes, for example, a processor and a memory as a hardware resource. Specifically, the processing circuitry 37 reads out a program stored in the storage circuitry 33 and expands it in the memory to execute various functions in accordance with the expanded program.

The processing circuitry 37 that realizes an image processing function 371 executes an image processing program corresponding to various types of image processing. Specifically, the processing circuitry 37 generates a rendering image by performing rendering processing on the volume data. The rendering image is a three-dimensional image such as a surface rendering image or a volume rendering image. The processing circuitry 37 generates a multi-planar reconstruction (MPR) image as a two-dimensional image by performing MPR processing on the volume data. In the case where the volume data has a plurality of heart chambers, the processing circuitry 37 divides the volume data into volume data of each heart chamber by a predetermined means such as threshold processing. Here, based on the divided volume data, the processing circuitry 37 generates a three-dimensional image of each heart chamber. The processing circuitry 37 that realizes the image processing function 371 corresponds to an image processing unit.

The processing circuitry 37 that realizes an analysis function 373 acquires an analysis result by analyzing the medical image regarding each of the heart chambers (hereinafter referred to as a medical image group) in time series. The medical image group is, for example, a three-dimensional image of a heart chamber obtained in a time series or a two-dimensional image of the heart chamber obtained in a time series. Specifically, the processing circuitry 37 analyzes a wall motion of each heart chamber by applying a predetermined wall motion analysis to the medical image group for each heart chamber. The predetermined wall motion analysis is, for example, a two-dimensional wall motion tracking (WMT) or a three-dimensional WMT; however, is not limited thereto. By executing an analysis program regarding the analysis function 373, the processing circuitry 37 sets as an initial outline a plurality of formation points indicating an outline of a tunica intima of a heart wall and a plurality of formation points indicating an outline of a tunica externa of a heart wall on the medical image corresponding to a predetermined heart time phase from the medical image group. The initial outline may be automatically set by predetermined image processing, or may be set by the instruction of an operator through the input interface circuitry 13. The initial outline is also appropriately adjustable by the instruction of the operator through the input interface circuitry 13. The processing circuitry 37 that realizes the analysis function 373 then tracks positions of the formation points in the other medical images included in the medical image group in a time series from the medical image in which the initial outline is set.

The processing circuitry 37 that realizes the analysis function 373 calculates a value of various kinds of analysis parameters regarding the wall motion of the heart chamber based on the result of the tracking. The analysis parameters are, for example, various strains such as a longitudinal strain, or an arrival time of a radial strain of a heart chamber to a predetermined threshold (hereinafter referred to as peak arrival time). The processing circuitry 37 generates a surface rendering image, an MPR image, and a polar map, etc. to which a color phase corresponding to a value of the analysis parameter is mapped, and which are segmented. The segment is a segmented area of a heart wall recommended by the American Society of Echocardiography and the American Heart Association. The processing circuitry 37 acquires an image generated by such mapping as a analysis result of the wall motion of each heart chamber. The processing circuitry 37 may also generate, for example, a graph indicating a time change in the value of the analysis parameter in each of a plurality of segments as the analysis result. The processing circuitry 37 causes the storage circuitry 33 to store the generated analysis result. In the case where the medical data is collected in accordance with the scanning order, the processing circuitry 37 acquires the analysis result in accordance with the scanning order by analyzing the medical data in accordance with the scanning order. The processing circuitry 37 that realizes the analysis function 373 corresponds to an analysis unit.

It should be noted that the expression "processor" used in the above explanation means circuit, such as, a Central Processing Unit (CPU) or a Graphics Processing Unit (GPU), Application Specific Integrated Circuit (ASIC), a programmable logic device (for example, Simple Programmable Logic Device (SPLD), Complex Programmable Logic Device (CPLD), and Field Programmable Gate Array (FPGA)), etc.

The processor realizes various functions by reading out and executing the program stored in the memory circuitry 33. Instead of storing various programs on the memory circuitry 33, the various programs may be directly integrated into the circuit of the processor in the control circuitry 35 or in the processing circuitry 37. In this case, the processor realizes the various functions by reading out and executing the various programs integrated into the circuit.

The entire configuration of the ultrasound diagnostic apparatus 1 of the present embodiment has been explained above. In the case of realizing the various functions in the present ultrasound diagnostic apparatus by the medical processing apparatus, the medical processing apparatus 20 comprises the components shown inside the dotted frame of FIG. 1. Based on the above configuration, the ultrasound diagnostic apparatus 1 and the medical processing apparatus 20 of the present embodiment are configured to display the analysis result of the wall motion of the heart chamber in a desired layout by a simplified operation using an addition function 375 and a display control function 377 explained below. In the following, the display control function 377 will be explained after explaining the addition function 375.

The processing circuitry 37 that realizes the addition function 375 adds incidental information including information regarding the kind of each of a plurality of regions in the heart to the analysis result of each of the regions, the analysis result being obtained by analyzing medical data. The processing circuitry 37, for example, generates the incidental information based on various kinds of information regarding the wall motion analysis of the heart chamber. The incidental information is information indicating attributes of the analysis result, and includes information, etc. input/selected upon analysis of the wall motion. The processing circuitry 37 adds the incidental information including information regarding the kind of the heart chamber to the analysis result of each of the heart chambers obtained by analyzing the medical image. The processing circuitry 37 causes the storage circuitry 33 to store the analysis result to which the incidental information is added. The processing circuitry 37 that realizes the addition function 375 by executing a program regarding the addition function 375 corresponds to an addition unit. In the case where the medical data is collected in accordance with the scanning order, the processing circuitry 37 includes the information of the scanning order corresponding to the region within the incidental information as information of the kind of region. Then, the setting of the kind of region would become unnecessary.

The processing regarding the addition function 375 according to the present embodiment will be explained in detail using a flow chart. FIG. 2 is a flowchart showing an example of a processing procedure regarding the addition function 375. The processing corresponding to the addition function 375 in FIG. 2 is step Sa4 and step Sa5.

A medical image obtained in a time series is generated by transmitting/receiving an ultrasonic wave over a period of one or more heartbeats with respect to each of the heart chambers (step Sa1). Prior to the execution of the analysis function 373, a patient ID, the kind of heart chamber, an image mode, and an analysis parameter name, etc. are set. The kind of heart chamber indicates a heart chamber name of an analysis target. The image mode indicates each type of image to which a color phase corresponding to a value of the analysis parameter is mapped, which are a surface rendering image, an MPR image, and a polar map, etc.

The processing circuitry 37 realizing the analysis function 373 sets a plurality of formation points indicating an initial outline in a medical image of a predetermined heart time phase from the medical image obtained in the time series (step Sa2). Here, the predetermined heart time phase indicates a ventricular diastole, etc. The formation points are tracked across the medical images, and the value of the set analysis parameter is calculated.

The processing circuitry 37 realizing the analysis function 373 acquires the analysis result of the heart chamber based on the set image mode and the value of the calculated analysis parameter (step Sa3). The analysis result is acquired for each heart chamber. In the case where the analysis target is, for example, two kinds of heart chambers such as a first heart chamber and a second heart chamber, the analysis result acquired in step Sa3 becomes a first analysis result regarding the first heart chamber and a second analysis result regarding the second heart chamber. In other words, the first analysis result is acquired by analyzing a first medical image obtained in a time series regarding the first heart chamber among a plurality of regions, and the second analysis result is acquired by analyzing a second medical image obtained in a time series regarding the second heart chamber among a plurality of regions. In the case where the medical image (volume data) including the first heart chamber and the second heart chamber, and obtained in a time series, is collected, the first analysis result and the second analysis result are acquired by analyzing this volume data.

Various information regarding the wall motion analysis of the heart chamber is used to generate the incidental information which is added to each analysis result (step Sa4). As information indicating the attributes of the analysis results, the incidental information includes, for example, information regarding the kind of the heart chamber, information regarding the heart time phase, information regarding collection time and date of the medical image, information regarding a phase of a stress echo at which the medical image is collected, information regarding a treatment progress of at least one of the heart chambers, and information regarding the image mode of the analysis result. In the case where the analysis target is, for example, two kinds of heart chambers such as the first heart chamber and the second heart chamber, a first incidental information to be added to the first analysis result and a second incidental information to be added to the second analysis result will be generated.

FIG. 3 shows an example of the incidental information generated by the processing circuitry 37. As shown in FIG. 3, the attributes included in the incidental information are the patient ID, the kind of the heart chamber, the collection date and time, the phase of the stress echo, the treatment progress, the image mode, and the analysis parameter name, etc. The collection date and time indicates a date and time of when the volume data of the analysis target was collected. The phase of the stress echo indicates a point of time the volume data was collected when executing the stress echo, which is, for example, before, during, and after applying stress. The treatment progress indicates, for example, information before and after treatment performed by a cardiac resynchronization therapy (CRT) for the heart chamber. In general, a column of the kind of heart chamber in FIG. 3 indicates a kind of region.

The generated incidental information is added to the analysis result and is stored in the storage circuitry 33 together with the analysis result (step Sa5). The processing circuitry 37 that realizes the addition function 375 adds, for example, the incidental information including information regarding the kind of region to the analysis result of each of the regions in the heart, the analysis result being obtained by analyzing medical data. Specifically, the processing circuitry 37 adds the first incidental information including information identifying a first region to the first analysis result corresponding to the first region among the regions, and adds the second incidental information including information identifying a second region to the second analysis result corresponding to the second region among the regions. Each of the attributes of the incidental information in FIG. 3 may be managed by, for example, a private tag of digital imaging and communication in medicine (DICOM) or a standard tag. The processing circuitry 37 may also generate, based on the incidental information, a management table for uniformly managing the created incidental information. The management table links each of the incidental information added to the analysis result by various attributes included in the incidental information.

The processing circuitry 37 realizing the display control function 377 determines a display position of the analysis results of each of the regions based on the incidental information. The processing circuitry 37, for example, displays the first analysis result in a first section among a plurality of sections in a screen of the display 15 based on the first incidental information, and displays the second analysis result in a second section among the sections based on the second incidental information. Specifically, the processing circuitry 37 determines a display position (section) of the analysis result to be displayed in a display area of the display 15, based on the kind of the heart chamber in the incidental information and an anatomical positional relationship of the heart chambers. Here, the display position of the analysis result corresponds to an anatomical position of the heart chamber. The processing circuitry 37 may determine the display position by further using at least one of the order in which the analysis result was selected by an operator, storage date of the analysis result, storage date of the volume data, and collection date and time of the volume data. The processing circuitry 37 may also determine the display position so that the analysis results obtained at different times (time phases) are arranged in parallel on the left and right of the display area by further using attributes such as before and after applying stress in the stress echo, and before and after treatment, etc. in the incidental information. The processing circuitry 37 may determine the display position inside the display area of each of a plurality of displays. In the case where, for example, four displays are adjacent to each other in a latticed pattern, the processing circuitry 37 determines which analysis result is to be arranged in the display area of each of the displays based on the incidental information. In the case where the scanning order is included in the incidental information, the processing circuitry 37 determines the display position of the analysis result in accordance with the anatomical positional relationship of the region based on the scanning order in the incidental information. Here, the analysis result is synchronized with the heart time phase and displayed in series at the display position in accordance with the scanning order, that is, the order in which the analysis result is generated.

Figure 4:
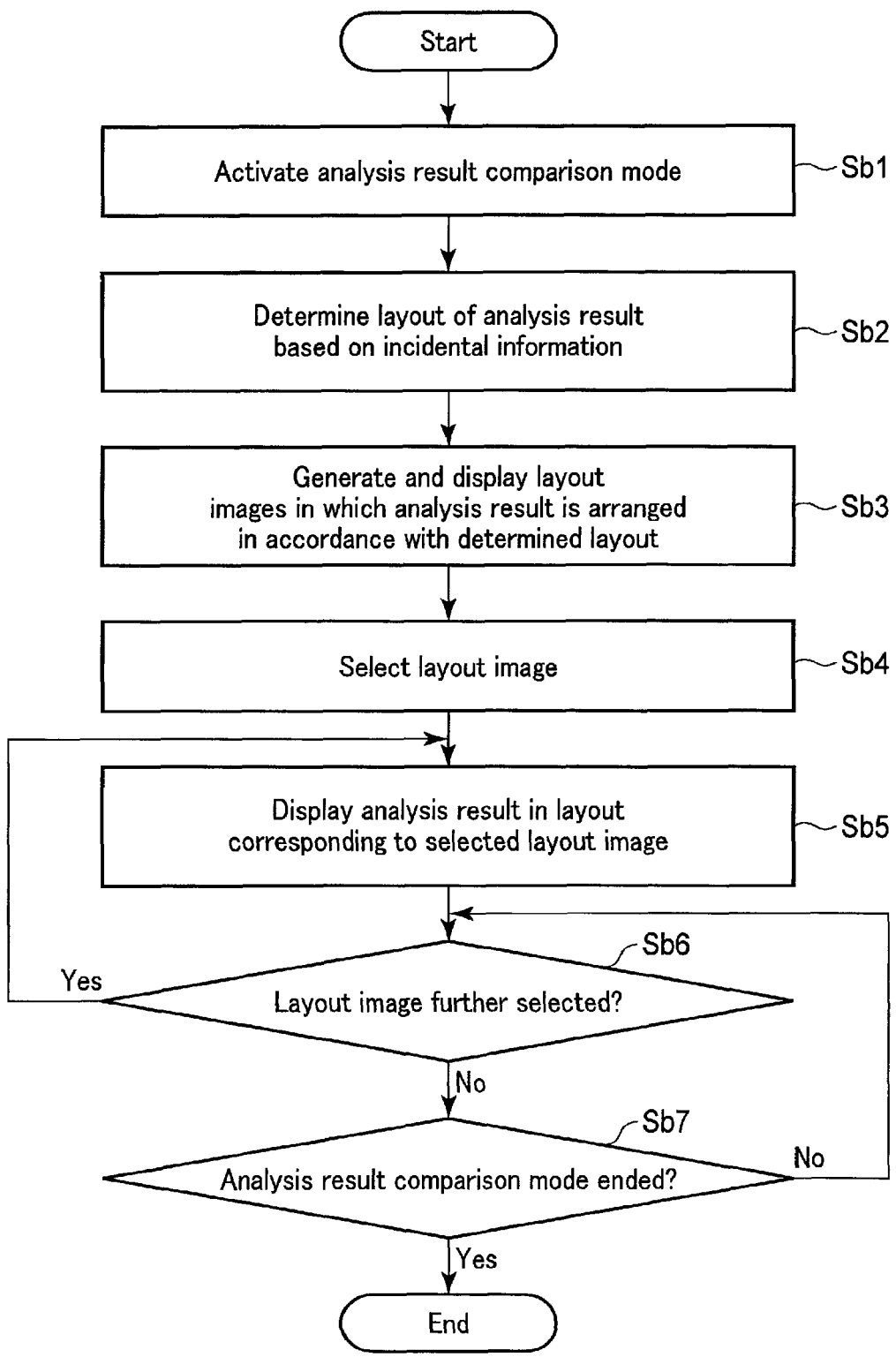
FIG. 4 is a flowchart showing an example of a processing procedure regarding a display control function in the present embodiment.

The processing regarding the display control function 377 according to the present embodiment will be explained in detail using a flow chart. FIG. 4 is a flowchart showing an example of a processing procedure regarding the display control function 377.

Based on an instruction from the operator, an analysis result comparison mode is activated (step Sb1). The analysis result comparison mode is a mode for displaying a plurality of analysis results on a display area of the display 15 in order to compare the analysis results. In step Sb1, a program corresponding to the display control function 377 is read out from the storage circuitry 33 and is executed. At such time, the processing circuitry 37 functions as a display control unit.

The layout of the analysis results in the display area of the display 15 is determined based on the incidental information (step Sb2). The layout of the analysis results corresponds to, for example, a template that shows which analysis result is to be arranged in which position of the display area at which size. The attributes of the incidental information for determining the layout are the analysis parameters regarding the analysis results, the image mode, the time information, spatial information, and patient information, as shown in FIG. 3. Specifically, the processing circuitry 37 determines a plurality of layouts in accordance with the purpose of comparison of the analysis results, such as a spatial comparison based on the anatomical positional relationship of the heart chambers, a temporal comparison, a phase comparison of the stress echoes, a comparison before and after treatment, a comparison between different image modes, and a comparison between different analysis parameters by using the attributes included in the incidental information in each of the analysis results. The layouts correspond to any combination of the analysis results useful for various comparisons of the analysis results. The layout may be an arrangement of the analysis results with different collection dates and times in one heart chamber, or an arrangement of the analysis results with different image modes in one heart chamber. The layout may also be determined using the incidental information and the management table.

The processing circuitry 37 realizing the display control function 377 generates a thumbnail image (hereinafter referred to as a layout image) in which the analysis results are arranged in accordance with the determined layout, and lists the layout image on the display 15 (step Sb3). The content of the layout image is not limited to the thumbnail of the analysis result, and may be literal information indicating the attribute of the analysis result. Instead of the layout image, the processing circuitry 37 may display a user interface such as a dialog box for inputting the attribute of the analysis result regarding various comparisons on the display 15. Here, the operator is able to input, for example, an image mode including at least one of the two-dimensional image and the three-dimensional image as the image mode of the analysis results.

When the layout image is selected (step Sb4), the processing circuitry 37 realizing the display control function 377 determines a layout corresponding to the selected layout image. When an attribute of the analysis result regarding various comparisons is input instead of selecting the layout image, the processing circuitry 37 may determine a layout that coincides with the input attribute from the layouts. The processing circuitry 37 displays the analysis result in the determined layout (step Sb5). The processing circuitry 37 synchronizes the analysis results of the heart chambers based on the heart time phase in the incidental information and displays them in moving images. Here, in the case where the image mode is the surface rendering image, the processing circuitry 37 may control the display 15 in order to rotate the analysis results in accordance with the instruction from the operator. In the following, a display example and layout of the analysis results in step Sb5 will be explained.

Figure 5:
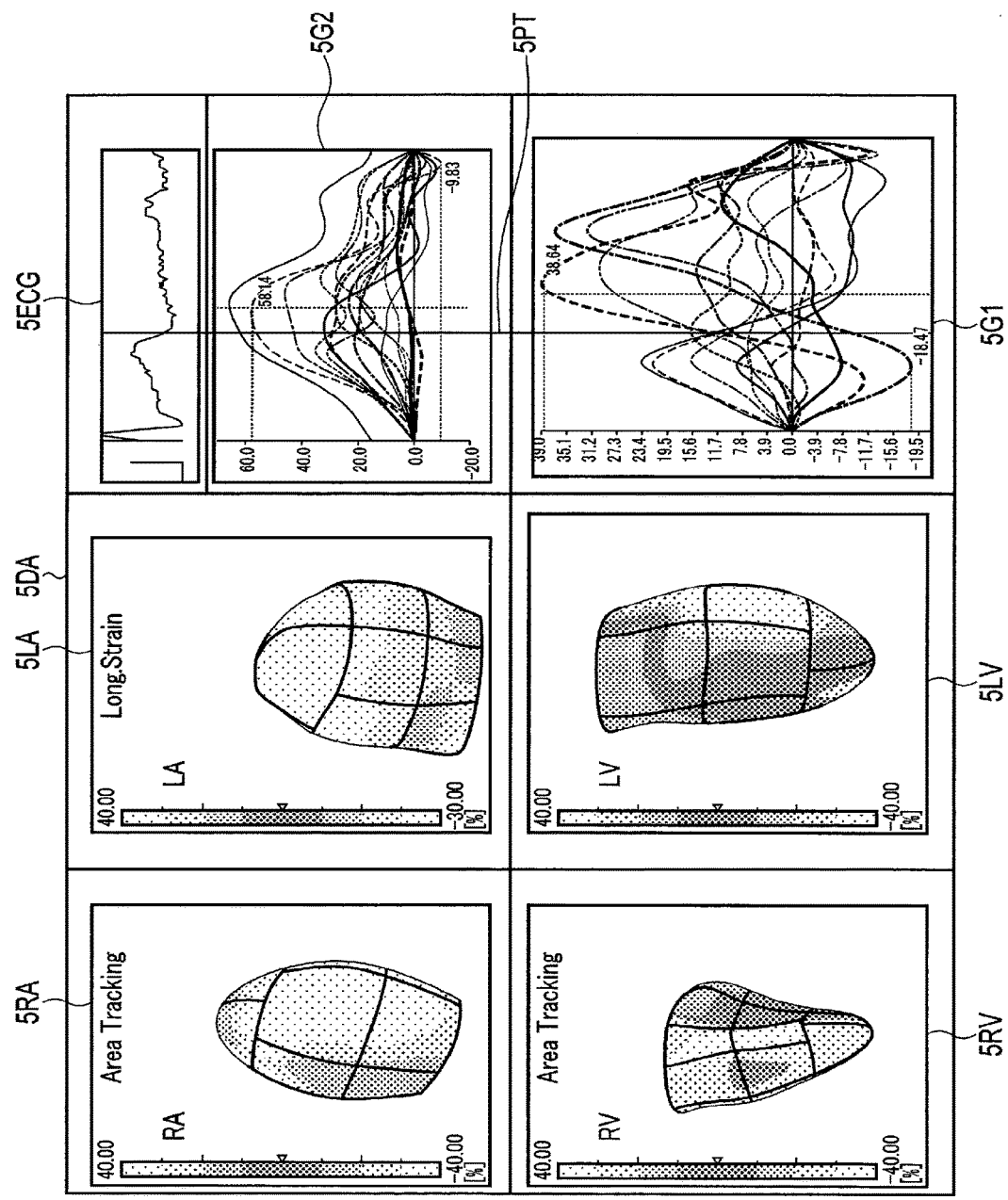
FIG. 5 shows a display example of analysis results of four chambers in the present embodiment.

FIG. 5 shows a display example (tile display) of the analysis results in the case where there are four heart chambers of the analysis target, and the image mode is a surface rendering image. 5RA shown in FIG. 5 shows a surface rendering image of the right atrium to which a color phase in accordance with a value of an analysis parameter of the right atrium is mapped. 5RV shown in FIG. 5 shows a surface rendering image of the right ventricle to which a color phase in accordance with a value of an analysis parameter of the right ventricle is mapped. 5LA shown in FIG. 5 shows a rendering image of the left atrium to which a color phase in accordance with a value of an analysis parameter of the left atrium is mapped. 5LV shown in FIG. 5 shows a rendering image of the left ventricle to which a color phase in accordance with a value of an analysis parameter of the left ventricle is mapped. In the four rendering images showing the analysis results, a curved line showing a boundary of a segment is displayed. The display positions of the analysis results 5RV, 5RA, 5LV, and 5LA remain to be in an anatomical positional relationship. The display positions of the analysis results 5RV, 5RA, 5LV, and 5LA are not limited to those shown in FIG. 5, and, may, for example, be associated with a position of an ultrasonic probe. At this time, in FIG. 5, the analysis result of the RV is displayed in an upper left field of a display area 5DA, the analysis result of the RA is displayed in a lower left field in the display area 5DA, the analysis result of the LV is displayed in a middle upper field of the display area 5DA, and the analysis result of the LA is displayed in a middle lower field of the display area 5DA. The analysis results 5RV, 5RA, 5LV, and 5LA are synchronized and reproduced as moving images based on the heart time phase in the incidental information.

Graphs 5G1 and 5G2 in FIG. 5 show time change in the values of the analysis parameters for each segment. 5PT in FIG. 5 is a bar that shows the heart time phases of the analysis results 5RV, 5RA, 5LV, and 5LA. The bar 5PT moves along a time axis of the graphs 5G1 and 5G2 and the electrocardiogram 5ECG in accordance with the heart time phase of the analysis results in the moving display of the analysis results. When the bar 5PT is instructed by the operator to move along the horizontal axis of the graphs or the electrocardiogram, the analysis results 5RV, 5RA, 5LV, and 5LA are displayed as display results corresponding to the position of the moved bar based on the heart time phase in the incidental information and the heart time phase indicated by the moved bar.

Figure 6:
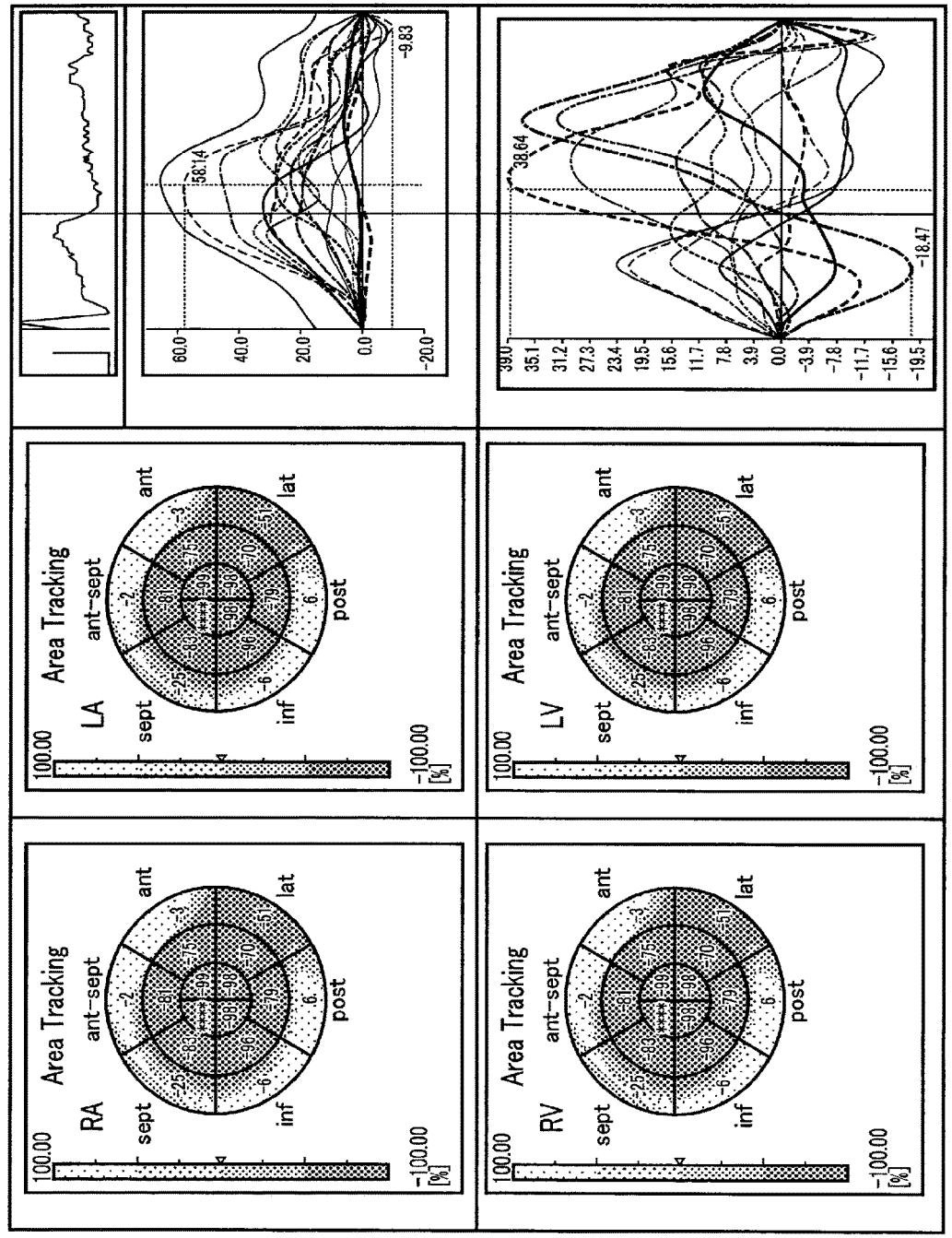
FIG. 6 shows another display example of the analysis results of the four chambers in the present embodiment.

FIG. 6 shows a display example (tile display) of the analysis result in the case where there are four heart chambers of the analysis target, and the image mode is a polar map. The difference between FIG. 5 and FIG. 6 is that the image modes are different, such as being a three-dimensional image or a polar map. In the polar map, curved lines and straight lines indicating the division of segments are displayed.

FIG. 7 shows a layout example of the analysis results in the case where there are four heart chambers of the analysis target, and the image mode is a short-axis tomographic image (two-dimensional image). SAX-B shown in FIG. 7 shows a display position of the short-axis tomographic image (SAX) of a base to which a color phase is mapped in accordance with the value of the analysis parameter. SAX-M shown in FIG. 7 shows a display position of the short-axis tomographic image of a mid cavity to which a color phase is mapped in accordance with the value of the analysis parameter. SAX-A shown in FIG. 7 shows a display position of the short-axis tomographic image (SAX) of an apical to which a color phase is mapped in accordance with the value of the analysis parameter. To the analysis result of SAX-A shown in FIG. 7, for example, the incidental information described in FIG. 3(a) is added. In a blank region 7BK of a display area 7DA in FIG. 7, a graph showing a temporal change of the values of the analysis parameters in the analysis results SAX-B, SAX-A, and SAX-M, an electrocardiogram, and a rendering image showing a cross-sectional position of the short-axis tomographic image regarding the analysis result, etc. are displayed.

FIG. 8 shows a layout example of the analysis results in the case where there are four heart chambers of the analysis target, and a three-dimensional image and a two-dimensional image co-exist as the image mode of the analysis results. RV3D in FIG. 8 shows a display position of the rendering image of the right ventricle to which a color phase is mapped in accordance with the value of the analysis parameter. RA2D in FIG. 8 shows a display position of the cross-sectional image of the right atrium to which a color phase is mapped in accordance with the value of the analysis parameter. LV3D in FIG. 8 shows a display position of the rendering image of the left ventricle to which a color phase is mapped in accordance with the value of the analysis parameter. LA2D in FIG. 8 shows a display position of the cross-sectional image of the left atrium to which a color phase is mapped in accordance with the value of the analysis parameter.

FIG. 5 to FIG. 8 are utilized when performing spatial comparison of the analysis results. FIG. 5 to FIG. 8 are examples of layouts of the analysis results regarding spatial comparison of the analysis results, and are not limited thereto. The layouts that are useful in spatial comparison of the analysis results obtained by, for example, combinations of other heart chambers and other image mode, etc. may also be determined based on the incidental information and the management table, etc. The number of analysis results displayed in one display area is not limited to four.

Figure 9:
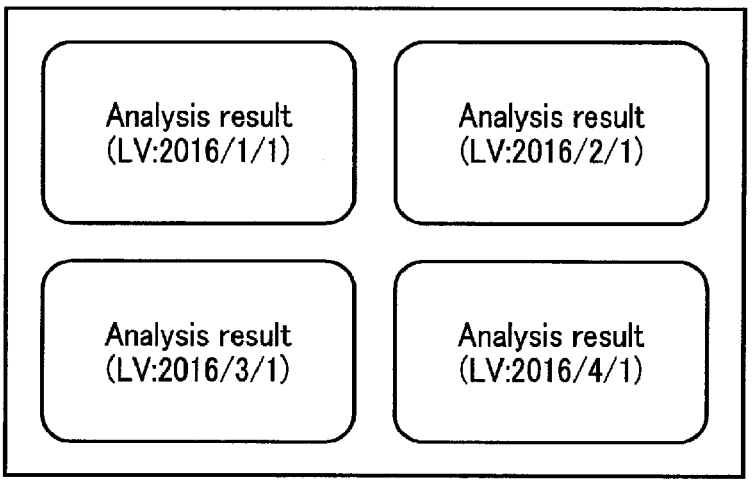
FIG. 9 shows an example of a layout of analysis results regarding a temporal comparison in the present embodiment.

FIG. 9 shows a layout example of four analysis results with different collection dates and times in one heart chamber (left ventricle LV). Here, the layout of the analysis results is determined based on the collection date and time of the medical image used for analyzing the wall motion of the heart chamber. FIG. 9 is utilized when performing temporal comparison of the analysis result.

Figure 10:
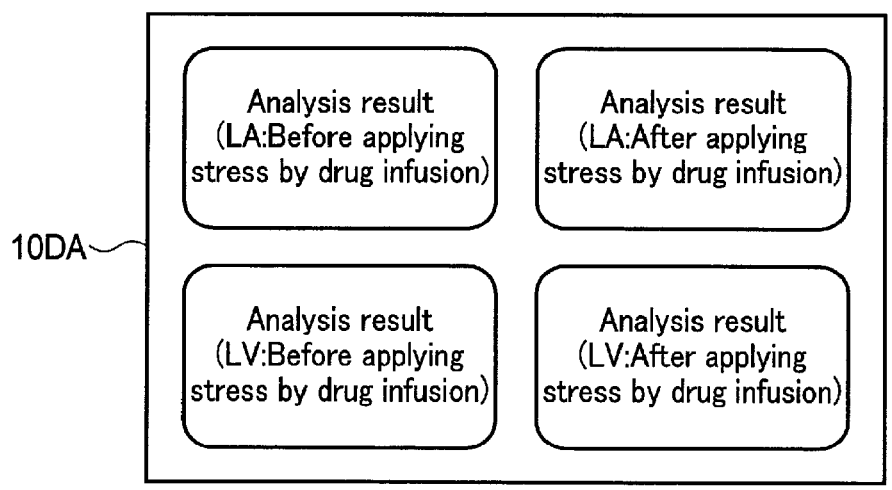
FIG. 10 shows an example of a layout of analysis results regarding comparison of two chambers before and after applying stress by a drug infusion in the present embodiment.

FIG. 10 shows a layout example of the analysis results for comparing phases of the stress echo (before and after applying stress by drug infusion) in two heart chambers (left ventricle LV and left atrium LA). As shown in FIG. 10, the display position of the analysis results regarding the left ventricle LV is determined as being on the lower part of a display area 10DA. The display position of the analysis results regarding the left atrium LA is determined as being on the upper part of the display area 10DA. The display position of the analysis results before applying stress by drug infusion is determined as being on the left side of the display area 10DA. The display position of the analysis results after applying stress by drug infusion is determined as being on the right side of the display area 10DA. Therefore, the layout of the analysis results is in an array shown in FIG. 10. Furthermore, four analysis results corresponding to four phases of the stress echo (before applying stress, two time phases when stress is being applied, and after stress has been applied, etc.) may be tile displayed for one heart chamber, such as the left ventricle LV.

FIG. 11 shows a layout example of the analysis results for comparing two heart chambers (left ventricle LV and right ventricle RV) before and after CRT treatment. As shown in FIG. 11, the display position of the analysis results regarding the left ventricle LV is determined as being on the right side of a display area 11DA. The display position of the analysis results regarding the right ventricle RV is determined as being on the left side of the display area 11DA. The display positions of the analysis results before CRT treatment is determined as being on the upper part of the display area 11DA. The display position of the analysis results after CRT treatment is determined as being on the lower part of the display area 11DA. Therefore, the layout of the analysis results is in an array shown in FIG. 11.

FIG. 12 shows a layout example of the analysis results for comparing different image modes of two heart chambers (left ventricle LV and left atrium LA). As shown in FIG. 12, the display position of the analysis results regarding the left ventricle LV is determined as being on the lower part of a display area 12DA. The display position of the analysis results regarding the left atrium LA is determined as being on the upper part of the display area 12DA. The display position of the analysis results using the surface rendering image as the image mode is determined as being on the left side of the display area 12DA. The display position of the analysis results using the polar map as the image mode is determined as being on the right side of the display area 12DA. To the analysis results on the lower right of FIG. 12, for example, the incidental information shown in FIG. 3(b) is added. Therefore, the layout of the analysis results is in an array shown in FIG. 12. The combination of the image modes is not limited to the rendering image and the polar map, and may also be combinations of other image modes.

FIG. 13 shows a layout example of the analysis results for comparing different analysis parameters of two heart chambers (left ventricle LV and left atrium LA). As shown in FIG. 13, the display position of the analysis results regarding the left ventricle LV is determined as being on the lower part of a display area 13DA. The display position of the analysis results regarding the left atrium LA is determined as being on the upper part of the display area 13DA. The display position of the analysis results indicating a longitudinal strain is determined as being on the left side of the display area 13DA. The display position of the analysis results indicating a peak arrival time is determined as being on the right side of the display area 13DA. To the analysis results on upper right of FIG. 13, for example, the incidental information shown in FIG. 3(c) is added. Therefore, the layout of the analysis results is in an array shown in FIG. 13.

FIG. 14 shows a layout example of four analysis results with different image modes in one heart chamber (left ventricle LV). In FIG. 14, LV 2D 4chView (apical four-chamber cross-sectional image), LV 2D 3chView (apical left ventricle longitudinal axis cross-sectional image), and LV 2D 2chView (apical two-chamber cross-sectional image) indicate the display position of the analysis results corresponding to three basic cross-sectional surfaces with respect to the left ventricle LV. LV 3D in FIG. 14 is a three-dimensional analysis result of the left ventricle that would correspond to the 4LV in FIG. 5, to which, for example, a cross-sectional position corresponding to the three basic cross-sectional surfaces is superimposed.

The layouts of the analysis results shown in FIG. 5 to FIG. 14 are only examples, and are not limited thereto. The thumbnails of FIG. 5 to FIG. 14 correspond to the layout images. When a further selection of the layout image is input (Yes in step Sb6), step Sb5 is executed. The analysis result is displayed until the analysis result comparison mode is ended (step Sb7).

According to the configurations mentioned above, the following effects may be obtained.

According to the ultrasound diagnostic apparatus 1 and the medical processing apparatus 20 of the present embodiment, the incidental information including information regarding the kind of the heart chamber is added to the analysis result of each of the heart chambers obtained by analyzing the medical image, and the display position of the analysis result can be determined based on the incidental information. According to the present embodiment, the display position can be determined inside the display area of the screen of a display 15, or inside a display area of the screens of a plurality of displays.

In the case where the analysis results are the first analysis result regarding the first heart chamber and the second analysis result regarding the second heart chamber, for example, the first analysis result can be acquired by analyzing a first time series image (first volume data), and the second analysis result can be acquired by analyzing a second time series image (second volume data) which is different from the first time series image. Alternately, by analyzing a common time series image (volume data) regarding the first heart chamber and the second heart chamber, the first analysis result and the second analysis result can be acquired. Therefore, the analysis results can be analyzed for each heart chamber in accordance with the acquired volume data. Subsequently, by adding the first incidental information to the first analysis result, and adding the second incidental information to the second analysis result, the display position of the first analysis result can be determined based on the first incidental information, and the display position of the second analysis result can be determined based on the second incidental information. Therefore, the analysis results can be arranged and displayed in the display area of the screen of the display 15 in accordance with the kind of heart chamber, that is, the anatomical positional relationship of the heart chambers.

According to the present embodiment, since the information on the heart time phase can be included in the incidental information, the analysis results of the heart chambers can be synchronized and displayed based on the incidental information. Therefore, since the analysis results can be synchronized and displayed in moving images in accordance with the operator's instruction, diagnostic efficiency can be improved.

Furthermore, according to the present embodiment, information of the scanning order corresponded to a region as information of the kind of region is included in the incidental information, and the analysis results can be acquired in accordance with the scanning order by analyzing the medical data collected in accordance with the scanning order. Based on the scanning order in the incidental information, the display position of the analysis results can be determined along the anatomical positional relationship of the regions. Therefore, it would be unnecessary to set (input) the kind of the region, which would improve convenience of the analysis result comparison mode, and improve diagnostic efficiency.

As explained above, according to the present embodiment, by uniform processing using the incidental information of the analysis result, that is, the processing related to the function for uniformly displaying the analysis result, the analysis result of the wall motion of the heart chamber can be displayed in a desired layout by a simple operation. In other words, when displaying the analysis results of the wall motion, it would become unnecessary to perform various inputs such as an input for selecting analysis results that have different anatomical positional relationships and have the same attribute for other matters, and an input for selecting analysis results that have different time relationships and have the same attribute for other matters. This would reduce the complexity and burden of setting the comparative display of the analysis results. In addition, without complicated input, the two-dimensional analysis result and the three-dimensional analysis result can be displayed in a co-existing manner. Thus, according to the present embodiment, local wall motion analysis can be simplified, which would improve diagnostic efficiency.

(First Modification)

The difference from the above-mentioned embodiment is that, in the case where an analysis result includes an image showing the contour of a region of an analysis target, processing circuitry 37 realizing an image processing function 371 merges images corresponding to each region based on incidental information. Specifically, in the case where the analysis result is an image showing the contour of a heart chamber (for example, a surface rendering image) to which a color phase corresponding to a value of an analysis parameter indicating movement of the heart chamber is mapped, analysis results of the heart chambers are merged based on the anatomical positional relationship of the heart chambers to generate a composite image.

The processing circuitry 37 realizing the image processing function 371 generates a composite image by merging the analysis results of the heart chambers based on the anatomical positional relationship of the heart chambers. The composite image is generated, for example, in response to an instruction from an operator. Specifically, the processing circuitry 37 acquires the coordinate of each segment of surface rendering images corresponding to each of the heart chambers. Based on the coordinate of the segment, the processing circuitry 37 executes the registration of surface rendering images to which a color phase corresponding to a value of an analysis parameter indicating movement of the heart chamber is mapped. The registration of the surface rendering images is adjustable as appropriate by the operator's instruction. In the case where volume data including the heart chambers is generated, the processing circuitry 37 may execute the registration of the rendering images based on the position of each of the heart chambers in this volume data. The processing circuitry 37 displays the generated composite image on the display 15. In accordance with the operator's instruction, the processing circuitry 37 may control the display 15 to rotate the composite image in an appropriate rotational axis direction.

Based on the incidental information, the processing circuitry 37 may also combine the graphs corresponding to the analysis results. Specifically, the processing circuitry 37 generates a composite graph by combining a time-change curve of a global strain indicating an average strain of an entire cardiac muscle and a time-change curve of a volume of each of the heart chambers by synchronizing the heart time phases.

After the composite image is generated, the processing circuitry 37 realizing an addition function 375 generates composite incidental information by combining incidental information added to the analysis results regarding the composite image. The processing circuitry 37 adds the composite incidental information to the composite image and stores it in the storage circuitry 33.

Figure 15:
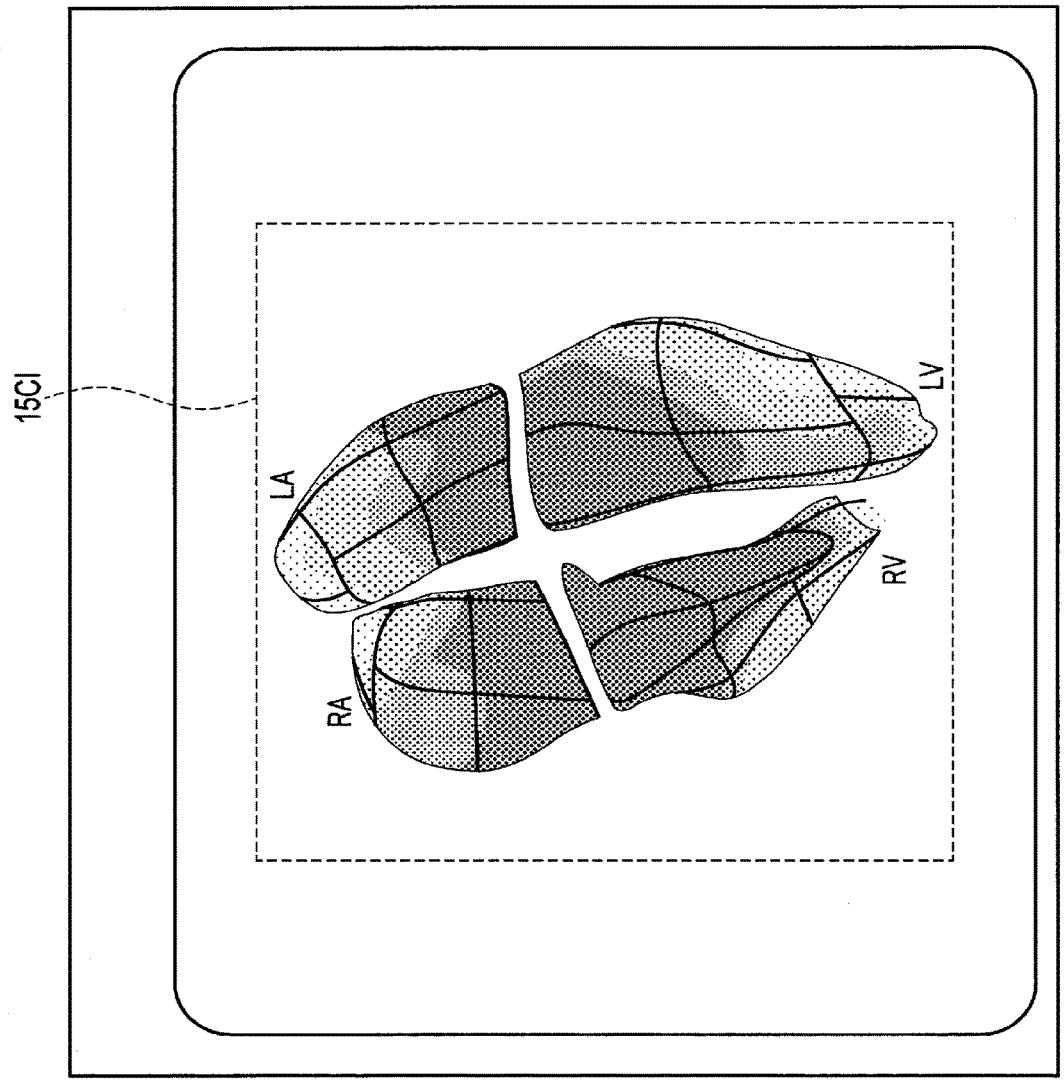
FIG. 15 shows an example of a composite image obtained by combining analysis results of four chambers in a first modification of the present embodiment.

FIG. 15 shows an example of a composite image 15CI which is obtained by combining the surface rendering images in the analysis results of four chambers as shown in FIG. 5. As shown in FIG. 15, the four surface rendering images corresponding to the four chambers are positioned and combined, and displayed as the composite image 15CI. Here, the composite image 15CI is displayed as a moving image by an operator's instruction. A composite graph may also be displayed beside the composite image 15CI. A variety of graphs and electrocardiograms may also be displayed together with the composite image 15CI.

As shown in FIG. 10, FIG. 11, and FIG. 13, a composite image may be generated for the analysis results of two chambers. Here, in FIG. 10, a composite image of LV and LA before applying stress by drug infusion is displayed on the left half of the display area, and a composite image of LV and LA after applying stress by drug infusion is displayed on the right half of the display area. In FIG. 11, a composite image of RV and LV before CRT is displayed on the lower half of the display area, and a composite image of RV and LV after CRT is displayed on the upper half of the display area. In FIG. 13, a composite image of a longitudinal strain by combining LV and LA is displayed on the left half of the display area, and a composite image of a peak arrival time combining LV and LA is displayed on the right half of the display area.

According to the configurations mentioned above, the following effects may be obtained.

According to an ultrasound diagnostic apparatus 1 and a medical processing apparatus 20 of the present modification, in the case where the analysis result is an image showing a contour of a heart chamber to which a color phase corresponding to a value of an analysis parameter indicating movement of the heart chamber is mapped (for example, a surface rendering image), a composite image as a result of the analysis result can be generated by merging the analysis results of the heart chambers based on the anatomical positional relationship of the heart chambers. Since the present modification allows the composite image to be rotated and displayed in any axial direction in accordance with the operator's instruction, the operator is capable of ascertaining the overall analysis results of the heart chambers. By merging the graphs corresponding to the analysis results, a composite graph can be generated. Therefore, according to the present modification, an entire image of the analysis results obtained by analyzing the wall motion of the heart chamber can be displayed by a simplified operation, thereby reducing a burden on the operator and improving diagnostic efficiency.

(Second Modification)

The difference from the embodiment mentioned above is that a display 15 is controlled switchable among a display position determined based on the kind of the heart chamber and the collection date and time, a display position determined based on the kind of the heart chamber and a phase of a stress echo, a display position determined based on the kind of the heart chamber and treatment progress, and a display position determined based on the kind of the heart chamber and an image mode of an analysis result.

The processing circuitry 37 that realizes a display control function 377 switches among the display positions determined based on the kind of the heart chamber and the collection date and time, the display position determined based on the kind of the heart chamber and a phase of a stress echo, the display position determined based on the kind of the heart chamber and treatment progress, and the display position determined based on the kind of heart chamber and the image mode of an analysis result. In other words, the processing circuitry 37 controls the display 15 in a manner so that the above switching is executable. Specifically, the processing circuitry 37 generates a plurality of tabs that correspond to each type of layout of the analysis results determined based on incidental information. The tabs are, for example, "Tile" that tile displays the analysis results corresponding to the heart chambers in accordance with an anatomical positional relationship as shown in FIG. 5 to FIG. 8, and FIG. 14, "Comp" that displays time comparison of the analysis results of the heart chambers, and "Merge" that displays a composite image of the analysis results as shown in FIG. 9 to FIG. 13, etc. The tabs may also include a tab (referred to as a reanalysis tab) that displays a screen for re-executing wall motion analysis for volume data of each of the heart chambers by resetting an initial outline, etc. Instead of displaying the reanalysis tab, a screen for re-executing the wall motion analysis may be displayed in response to a double-click operation on the displayed analysis result. In the case where there are a plurality of combinations (layouts) of display positions of the analysis results corresponding to the above tabs, the processing circuitry 37 may generate tabs in a hierarchically associated manner in accordance with the combination of various attributes included in the incidental information. Here, the processing circuitry 37 hierarchically manages the layout in accordance with various attributes included in the incidental information.

The processing circuitry 37 switches the display position of the analysis result in accordance with the choice of tab, and displays the analysis results on the display 15. In other words, the processing circuitry 37 controls the display 15 to switch the layout of the analysis results before the tab was chosen to a layout of the analysis results corresponding to the chosen tab.

FIG. 16 shows a state in which a Tile tab is chosen, and a display example of displaying the analysis results of four chambers that are tile displayed and graphs together with a plurality of tabs. Tabs LV, LA, RV, and RA in FIG. 16 indicate tabs for displaying screens regarding the re-execution of the wall motion analysis. In FIG. 16, for example, when a Merge tab is chosen, for example, the composite image shown in FIG. 15 is displayed. Here, the Merge tab is highlighted, and the Tile tab becomes a standard display.

Instead of generating tabs, the processing circuitry 37 may also display the layout images together with the analysis results. In such case, analysis results corresponding to the chosen layout image are displayed on the display 15.

Figure 17:
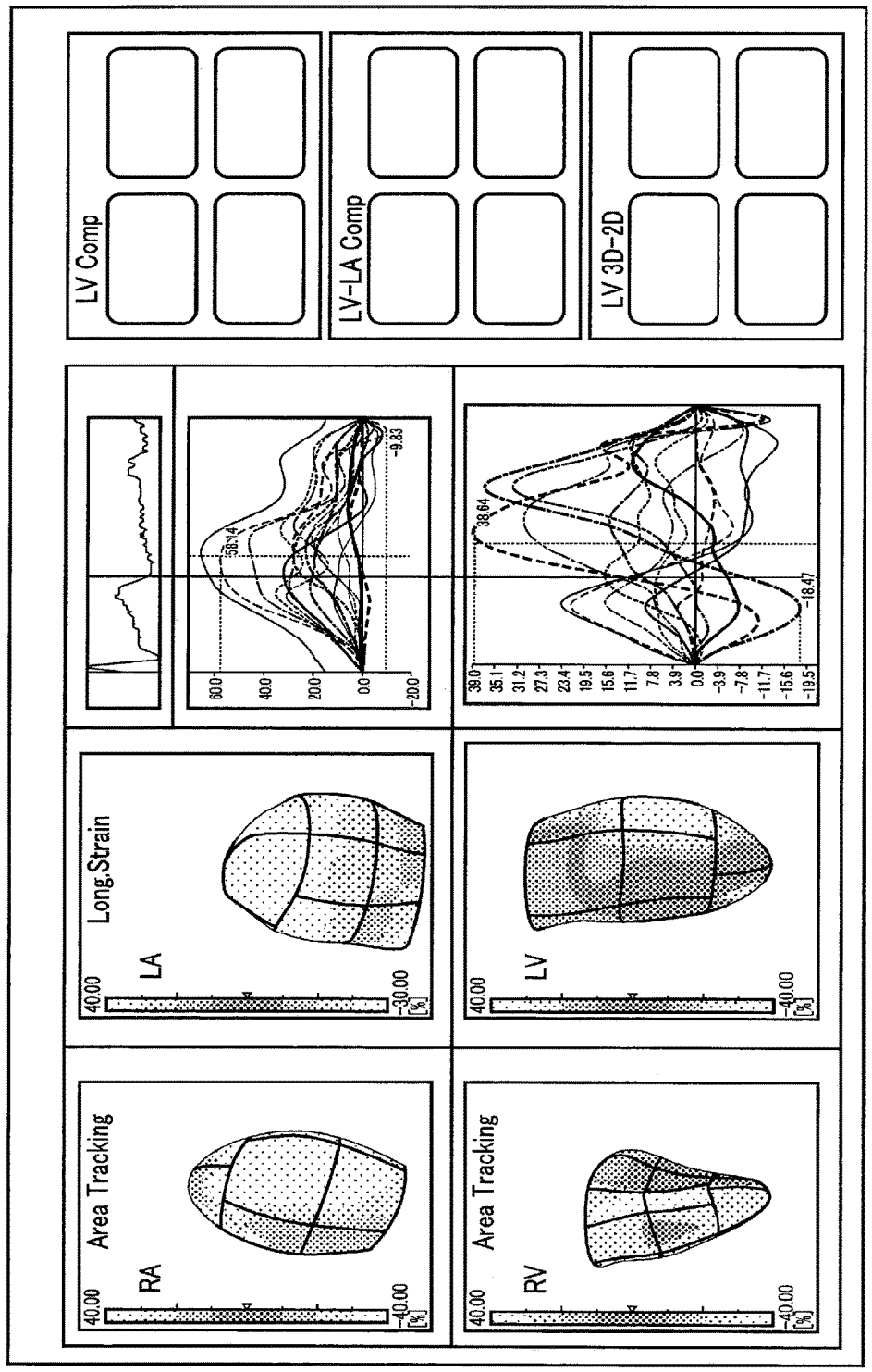
FIG. 17 shows a display example of displaying analysis results together with a plurality of layout images in the second modification of the present embodiment.

FIG. 17 shows a display example of displaying layout images together with the analysis results. An LV Comp in FIG. 17 is, for example, a layout image corresponding to the time comparison of the analysis results of the left ventricle LV shown in FIG. 9. An LV-LA Comp in FIG. 17 is, for example, a layout image corresponding to the time comparison of the analysis results between the left ventricle LV and the left atrium LA shown in FIG. 10, FIG. 12, and FIG. 13. An LV 3D-2D in FIG. 17 is, for example, a layout image corresponding to a mixed display of the three-dimensional image and the second-dimensional image regarding the analysis results of the left ventricle LV shown in FIG. 14.

According to the configurations mentioned above, the following effects may be obtained.

According to the ultrasound diagnostic apparatus 1 and the medical processing apparatus 20 of the present modification, information regarding the collection time and date of the medical image, information regarding a phase of a stress echo in which the medical image is collected, information regarding treatment progress of at least one of a plurality of heart chambers, and information regarding the image mode of the analysis result, can be further included in the incidental information. Therefore, the processing circuitry 37 can control the display 15 to be switchable among a display position determined based on the kind of the heart chamber and the collection date and time, a display position determined based on the kind of the heart chamber and a phase of a stress echo, a display position determined based on the kind of the heart chamber and treatment progress, and a display position determined based on the kind of the heart chamber and the image mode of the analysis result. For example, the present modification can switch the display formation of the analysis results in accordance with the choice of tab or layout image displayed together with the analysis results. Therefore, the analysis results obtained by analyzing the wall motion of the heart chamber can be displayed by a simplified operation of choosing a tab or a layout image. Furthermore, it is possible to re-execute the wall motion analysis of the heart chamber when the analysis results are being displayed. The present modification allows simple re-execution of the wall motion analysis when the analysis results are being displayed.

Therefore, according to the present modification, the burden on the operator can be reduced when displaying the analysis result of the wall motion in a desired layout, thereby improving diagnostic efficiency.

(Third Modification)

The present modification adopts the processing of the second modification for a composite image. In the present modification, since each processing executed by the processing circuitry 37 can be understood by reading the analysis result in the second modification as the composite image as appropriate, detailed explanations will be omitted.

Figure 18:
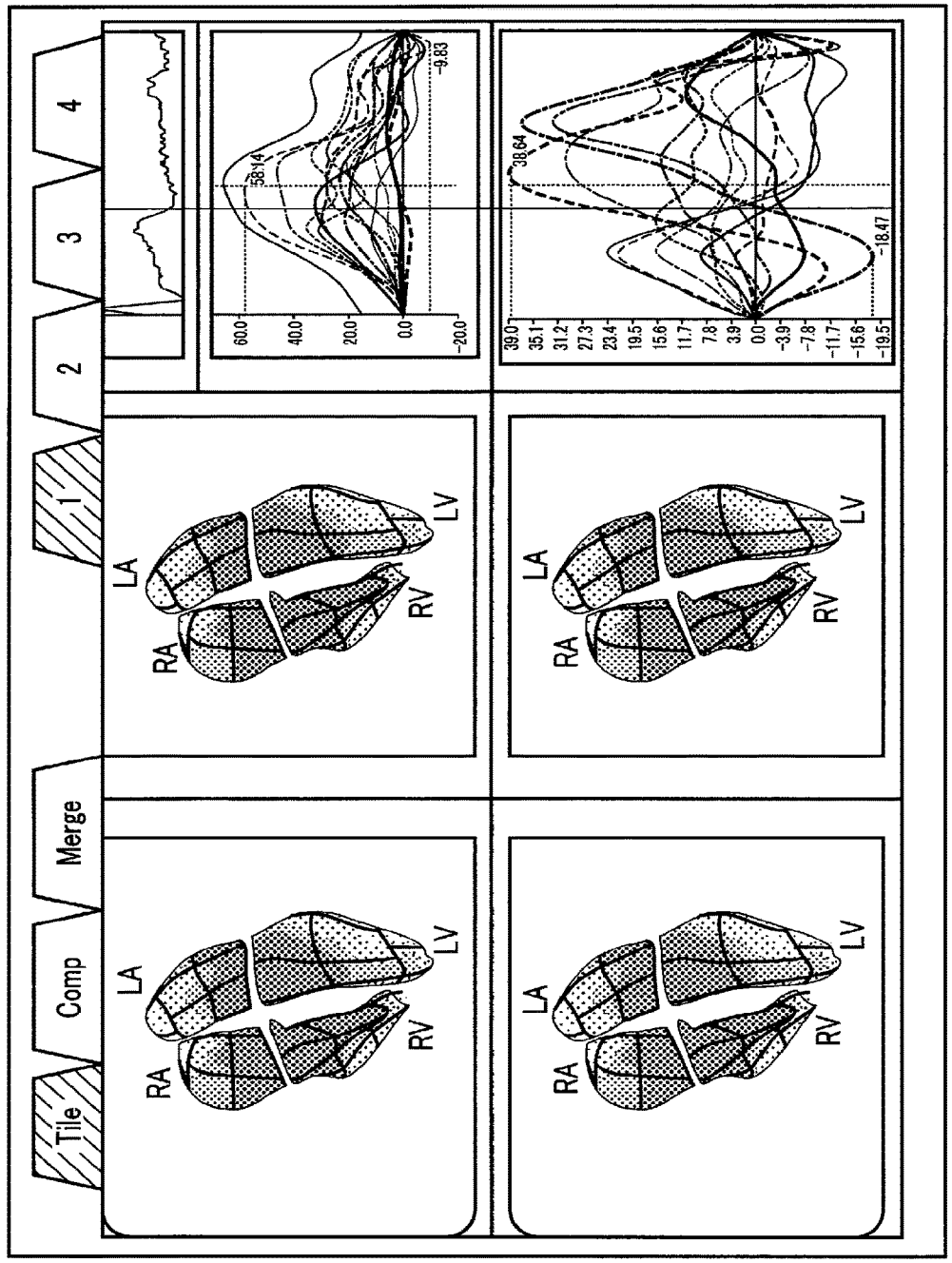
FIG. 18 shows an example of a comparative display of composite images obtained by combining analysis results of four chambers in a third modification of the present embodiment.

FIG. 18 is an example of a comparative display of a composite image (anatomical-merge) obtained by combining analysis results of four chambers. As shown in FIG. 18, tab 1, a Comp tab, and a Merge tab are highlighted. When a Tile tab is chosen, non-merged analysis results are tile displayed. Tab 1 is a tab indicating a comparative display of composite images in which four chambers are combined. Tab 2 is a tab indicating a comparative display of, for example, LVLA composite images in which the left ventricle and the left atrium are combined. Tab 3 is a tab indicating a comparative display of, for example, LVRV composite images in which the left ventricle and the right ventricle are combined. Tab 4 is a tab indicating a comparative display of, for example, three-chamber composite images in which the left ventricle, the left atrium, and the right ventricle are combined. As shown in FIG. 18, in accordance with the chosen tab, the merged composite images are switched between tile display and comparative display, etc.

The processing circuitry 37 generates, for example, a two-chamber composite image (left ventricle and left atrium composite image, left ventricle and right ventricle composite image) in which two chambers among four are composited. The processing circuitry 37 then controls the display 15 in accordance with the operator's instruction to perform comparative display of the two-chamber composite images before and after applying stress, and before and after treatment, etc. Since the tile display and comparative display according to the present modification are added to various composite images, they are different from the tile display and comparative display of the present embodiment, and have an embedded structure in which they are included in the category of the composite image.

According to the configurations mentioned above, the following effects may be obtained.

According to the ultrasound diagnostic apparatus 1 and the medical processing apparatus 20 of the present modification, effects of each of the present embodiment and the second modification can be obtained for the composite image. In other words, since a tile display and a comparative display of a composite image obtained by compositing a plurality of analysis results regarding a plurality of heart chambers can be displayed by a simplified operation, wall motion analysis becomes easier, which reduces the burden on the operator, and improves efficiency in diagnosing the analysis results.

(Fourth Modification)

The difference from the above-mentioned embodiment and modifications is that a plurality of regions in the heart includes at least a valve among a tricuspid valve, a pulmonary valve, a mitral valve, and an aortic valve as an analysis target.

Prior to the execution of the analysis function 373, the processing circuitry 37 realizing the addition function 375 sets a patient ID, the kind of valve of the analysis target, an image mode, and an analysis parameter name, etc. The kind of valve is, for example, a valve name, which is input by an operator's instruction through the input interface circuitry 13. The processing circuitry 37 includes the information of the set valve in the incidental information. In the incidental information of FIG. 3, the kind of valve is described in a column of the kind of region corresponding to a column of the kind of heart chamber.

The processing circuitry 37 realizing the analysis function 373 applies a predetermined valve motion analysis to a medical image group in each of the set valves to analyze movements of each of the valves. A predetermined valve motion analysis is, for example, a two-dimensional WMT or a two-dimensional WMT. The predetermined valve motion analysis is not limited to WMT, and may use, for example, various methods such as tissue Doppler imaging.

By executing an analysis program regarding the analysis function 373, the processing circuitry 37 sets, for example, a plurality of formation points indicating an outline of the inside of the valve and a plurality of formation points indicating an outline of the outside of the valve on the medical image corresponding to a predetermined heart time phase from the medical image groups as initial outlines. The processing circuitry 37 tracks positions of the formation points in other medical images included in the medical image groups in a time series from the medical image in which the initial outline is set. The processing circuitry 37 calculates a value of various analysis parameters regarding the valve motion based on the result of the tracking. The analysis parameters are, for example, in the mitral valve, a diastolic descent rate and a systolic anterior movement. The processing circuitry 37 generates a surface rendering image to which color phase corresponding to a value of the analysis parameter is mapped and an MPR image, etc. as images indicating the analysis result of the valve motion.

The processing circuitry 37 realizing the display control function 377, determines a display position (section) of the analysis result displayed in a display area of the display 15 as a layout based on the kind of region in the incidental information (the kind of heart chamber and the kind of valve) and an anatomical positional relationship of a plurality of regions (heart chambers and valves). Specifically, the display position of the analysis result in the layout corresponds to an anatomical position of the heart chamber and the valve. The processing circuitry 37 displays the analysis result of the valve in accordance with the determined layout.

Figure 19:
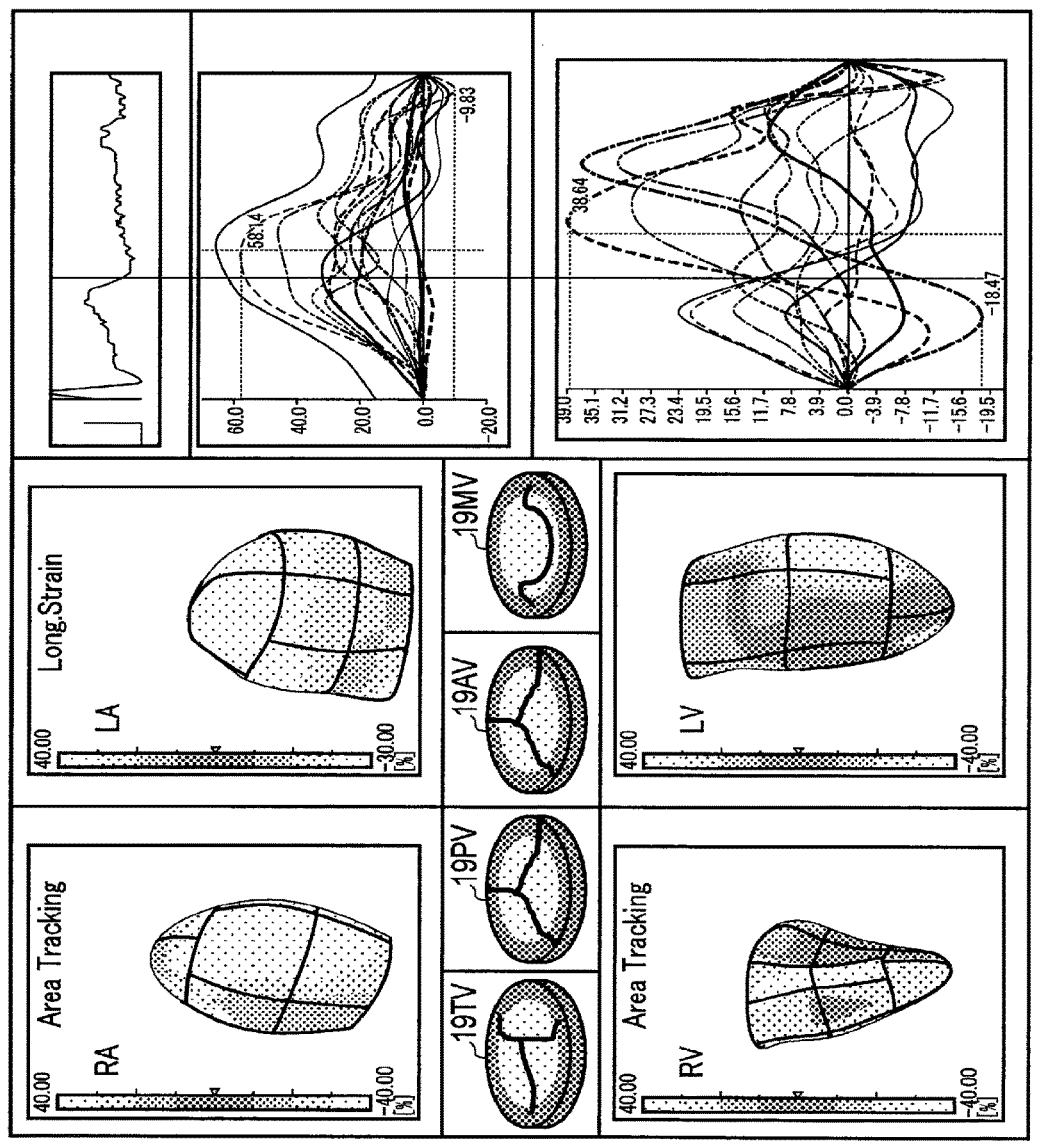
FIG. 19 shows a display example of analysis results of four chambers and four valves in a fourth modification of the present embodiment.

FIG. 19 shows a display example (tile display) of the analysis result in the case where the analysis targets are four heart chambers and four valves, and the image mode is the surface rendering image. The number of valves is not limited to four. 19MV shown in FIG. 19 shows a surface rendering image of the mitral valve to which a color phase corresponding to a value of an analysis parameter of the mitral valve is mapped. 19AV shown in FIG. 19 shows a rendering image of the aortic valve to which a color phase corresponding to a value of an analysis parameter of the aortic valve is mapped. 19PV shown in FIG. 19 shows a rendering image of the pulmonary valve to which a color phase corresponding to a value of an analysis parameter of the pulmonary valve is mapped. 19TV shown in FIG. 19 shows a rendering image of the tricuspid valve to which a color phase corresponding to a value of an analysis parameter of the tricuspid valve is mapped. FIG. 19 has a layout in which the analysis results of four valves are added to the display example of the analysis results of four chambers shown in FIG. 5 in accordance with the anatomical positional relationship of the four chambers and the four valves.

As an application of the present modification, the processing of the first modification can also be applied to the present modification. In the case where the display example shown in FIG. 19 is, for example, displayed on the display 15, the processing circuitry 37 realizing the image processing function 371 generates, for example, a composite image in response to the operator's instruction.

FIG. 20 shows an example of a composite image which is obtained by combining the surface rendering images showing the analysis results of the four chambers and the four valves shown in FIG. 19. As shown in FIG. 20, the registration for images of eight analysis results corresponding to four chambers (left ventricle LV, right ventricle RV, left atrium LA, right atrium RA) and four valves (mitral valve MV, aortic valve AV, pulmonary valve PV, tricuspid valve TV) is executed in the same heart time phase. A composite image generated for each heart time phase by this registration is displayed on the display 15. In FIG. 20, there is a space between the four chambers and the four valves; however, the four chambers and the four valves may be adjacent to each other in accordance with the anatomical positional relationship. Here, the transparency (or opacity) and the luminance value, etc. of each of the four chambers and the four valves may be adjusted by, for example, an operator's instruction to the scroll bar provided at the lower end of the composite image. In FIG. 20, four valves are described as an example; however, the number of valves displayed is not limited to four.

According to the configurations mentioned above, the following effects may be obtained.

According to the ultrasound diagnostic apparatus 1 and the medical processing apparatus 20 of the present modification, the analysis result of a valve of at least one of the tricuspid valve, the pulmonary valve, the mitral valve, and the aortic valve at a plurality of regions can be displayed on the display 15 together with the analysis results of the heart chambers in accordance with the anatomical positional relationship based on the incidental information. According to the present modification, the composite image can be displayed in a manner where the transparency and the luminance value of the four chambers and the four valves are adjustable.

As explained above, according to the present modification, by uniform processing using the incidental information added to the analysis result, that is, the processing related to the function of uniformly displaying the analysis result, the analysis results of a plurality of regions including a plurality of heart chambers and a plurality of valves in the heart can be displayed by a simplified operation, while maintaining the anatomical positional relationship. Thus, the present modification simplifies diagnosis of a local wall motion analysis and diagnosis of a valve motion analysis, and improves diagnostic efficiency.

(Fifth Modification)

The difference from the above-mentioned embodiment and modifications is that an unified analysis result is acquired by unifying the medical data corresponding to adjacent regions selected by the operator among a plurality of regions, and the display position of the unified analysis result is determined based on the incidental information including information in which the adjacent regions are unified.

The input interface circuitry 13 inputs regions adjacent to each other (hereinafter, referred to as adjacent regions) among the regions by an operator's selection instruction. The input of the adjacent regions corresponds to the grouping of regions in the regions. The selecting instruction may be input at any time as long as it is, for example, before the processing in step Sb1 of the flowchart of FIG. 4. In the case where the operator wishes to obtain, for example, an analysis result of unifying the left ventricle and the right ventricle to diagnose malformation such as a ventricle septal defect or single ventricle, the left ventricle and the right ventricle are chosen among the regions. Furthermore, in the case where the operator wishes to obtain, for example, an analysis result of unifying the left ventricle and the left atrium to diagnose valvular disorder, etc. regarding the mitral valve, the left ventricle and the left atrium are chosen among the regions. The choice of region is not limited to the above explanation, and can be discretionarily selected as desired by the operator.

The processing circuitry 37 realizing the addition function 375 includes the information obtained by unifying the adjacent regions (hereinafter referred to as region unification information) into the incidental information. In the case where the left ventricle and the right ventricle are chosen, the column of the kind of heart chamber in the incidental information of FIG. 3 will indicate, for example, both ventricles. In the case where the left ventricle and the left atrium are chosen, the column of the kind of heart chamber in the incidental information of FIG. 3 will indicate, for example, a left side heart chamber.

The processing circuitry 37 realizing the analysis function 373 unifies medical images of the same heart time phase into medical data in a medical image group corresponding to adjacent regions. The processing circuitry 37 sets an initial outline regarding the adjacent regions. The processing circuitry 37 analyzes the unified medical data by using the initial outline to acquire an integration analysis result. For example, in the case where the left ventricle and the right ventricle are chosen, an analysis result for the entire ventricle of both ventricles obtained by unifying the left ventricle and the right ventricle is generated as the unified analysis result. Furthermore, in the case where the left ventricle and the left atrium are chosen, an analysis result for the entire heart chamber on the left side chamber obtained by unifying the left ventricle and the left atrium is generated as the unified analysis result.

The processing circuitry 37 realizing the display control function 377 determines a display position (section) of the unified analysis result on the display 15 based on the region unification information in the incidental information. The processing circuitry 37 causes the display 15 to display the unified analysis result at the determined display position.

Figure 21:
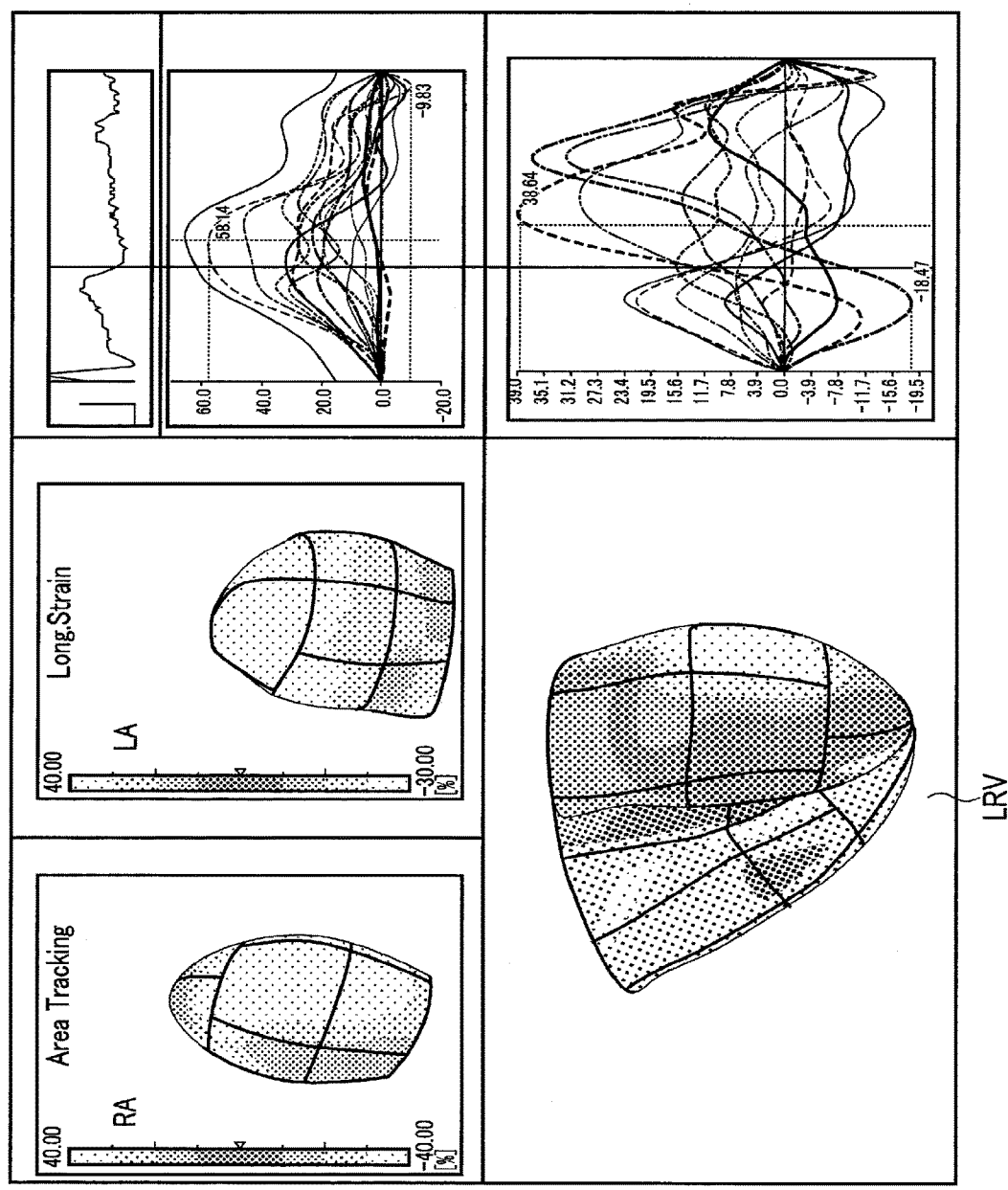
FIG. 21 shows an example of a unified analysis result LRV in a case where a left ventricle and a right ventricle are selected in a fifth modification of the present embodiment.

FIG. 21 shows an example of the unified analysis result LRV in a case where the left ventricle and the right ventricle are selected. As shown in FIG. 21, in the case where the left ventricle and the right ventricle are chosen by the operator, the unified analysis result LRV for the entire ventricle of both ventricles obtained by unifying the left ventricle and the right ventricle is displayed. In FIG. 21, other than the unified analysis result LRV, the analysis result of the right atrium RA and the analysis result of the left atrium LA, etc. are shown. However, it is also possible to display only the unified analysis result LRV. The regions that are unified and analyzed are not limited to two as shown in FIG. 21. The adjacent regions may, for example, be the heart chamber and the valve such as the left ventricle, the mitral valve, and the aortic valve.

According to the configurations mentioned above, the following effects may be obtained.

According to the ultrasound diagnostic apparatus 1 and the medical processing apparatus 20 of the present modification, the unified analysis result can be acquired by unifying and analyzing the medical data corresponding to the adjacent regions selected by the operator among a plurality of regions, and the display position of the unified analysis result can be determined based on the incidental information including information on the unified adjacent regions. Therefore, according to the present modification, not only the region of the malformed heart, but also the region selected by the operator's choice can be unified and analyzed.

Therefore, according to the present modification, even if at least one region of the regions is malformed, the unified analysis result can be displayed by a simplified operation while maintaining the anatomical positional relationship. Thus, the present modification simplifies the diagnosis of motion analysis in the regions of the heart, etc. and improves diagnostic efficiency.

(Sixth Modification)

The difference from the above-mentioned embodiment and modifications is that a region designated by an operator among a plurality of regions, and a region adjacent to the designated region are identified, and an image showing an analysis result corresponding to the identified region is merged.

The input interface circuitry 13 designates a region among the regions by an operator's instruction. The operator may input the designation of a region any time as long as it is, for example, before the processing in step Sb1 of the flowchart of FIG. 4.

The processing circuitry 37 realizing the image processing function 371 identifies the designated region (hereinafter referred to as the designated region) and a region adjacent to the designated region. The processing circuitry 37 generates a composite image by merging images showing the analysis results corresponding to the identified regions. The processing circuitry 37 displays the composite image on the display 15.

In the case where, for example, the left ventricle is designated, the composite image includes the analysis result of the left ventricle, the analysis result of the right ventricle, the analysis result of the mitral valve, and the analysis result of the aortic valve. Here, the composite image becomes, for example, an image which is obtained by combining the analysis result of the mitral valve and the analysis result of the aortic valve with the LRV in FIG. 21.

According to the configurations mentioned above, the following effects may be obtained.

According to the ultrasound diagnostic apparatus 1 and the medical processing apparatus 20 of the present modification, a region designated by the operator among a plurality of regions and a region adjacent to the designated region can be identified, and images showing analysis results corresponding to the identified regions can be merged. Therefore, according to the present modification, the analysis result of a region receiving attention from the operator (hereinafter referred to as region of interest), and the analysis result of a region adjacent to the region of interest, can be merged and displayed on the display 15. Thus, the present modification simplifies diagnosis of the motion analysis with a focus on the region of interest, etc., and improves diagnostic efficiency.

(Seventh Modification)

The difference from the above-mentioned embodiment and modifications is that, by including information regarding a disease name in the incidental information, a region related to the disease name and a region adjacent to the region related to the disease name are identified from the regions based on the incidental information, and images showing analysis results corresponding to the identified regions are merged.

The input interface circuitry 13 inputs a disease name by an operator's instruction. The disease name may be input at any time as long as it is, for example, before the processing in step Sb5 of the flowchart of FIG. 2.

The processing circuitry 37 realizing the addition function 375 includes information of the input disease name in the incidental information. The processing circuitry 37 incorporates information associating a region related to the disease name and a region adjacent to the region related to the disease name (hereinafter referred to as disease name related region information) into the incidental information. The information of the disease name and the disease name related region information are added in, for example, the incidental information of FIG. 3 as new attributes.

In response to the activation of an analysis result comparison mode, the processing circuitry 37 realizing the display control function 377 controls the display 15 so that, for example, the disease name is displayed in a dialog box. When the disease name is designated through the input interface circuitry 13, the processing circuitry 37 identifies a region related to the disease name and a region adjacent to the region related to the disease name from the regions based on the incidental information. The processing circuitry 37 merges images showing analysis results corresponding to the identified regions. In the present modification, in the case where the disease name is input before the processing of step Sb1, medical data regarding the identified regions may be unified to acquire the unified analysis result as in the fifth modification.

In the case where the disease name is, for example, an interventricular septal defect, when the disease name is designated through the input interface circuitry 13, the processing circuitry 37 realizing the display control function 377 identifies the left ventricle and the right ventricle. The processing circuitry 37 then generates a composite image by registration at the same heart time phase for an image showing an analysis result of the identified left ventricle and an image showing an analysis result of the identified right ventricle. The composite image corresponds to, for example, the LRV in FIG. 21.

According to the configurations mentioned above, the following effects may be obtained.

According to the ultrasound diagnostic apparatus 1 and the medical processing apparatus 20 of the present modification, by including information regarding a disease name in the incidental information, a region related to the disease name and a region adjacent to the region related to the disease name can be identified from the regions based on the incidental information, and images showing analysis results corresponding to the identified regions can be merged. Therefore, according to the present modification, the analysis results of the regions identified in accordance with the disease name regarding the heart can be merged and displayed on the display 15. Thus, the present modification simplifies diagnosis of the motion analysis with respect to the disease name of the heart, etc. and improves diagnostic efficiency.

(Eighth Modification)

The difference from the above-mentioned embodiment and modifications is that, by including a plurality of measurement values measured at a region in the incidental information, a region corresponding to a measurement value outside a reference range among the measurement values and a region adjacent to the region corresponding to the measurement value outside the reference range are identified from the regions, and images showing analysis results corresponding to the identified regions are merged.

In accordance with the operator's instruction, the input interface circuitry 13 inputs a plurality of measurements with respect to the regions of the heart in an ultrasonic image for measurement items in an echocardiographic examination. The measurements are, for example, a valve area of various valves, a diameter of various heart chambers, a wall thickness of various heart chambers, and various blood flow velocity waveforms in Doppler data.

The storage circuitry 33 stores a reference range with respect to each of the measurement values obtained by performing the measurements. The reference range, for example, corresponds to a range in which the measured measurement value is determined as normal, and is preset with respect to each of the measurements.

The processing circuitry 37 realizing the addition function 375 includes the measured measurement value and the name of the measurement item in the incidental information corresponding to the measured region. The measurement value is, for example, added in the incidental information in FIG. 3 as a new attribute. By this incidental information, the measurement value is corresponded to the region.

The processing circuitry 37 realizing the image processing function 371 identifies a measurement value that is outside the reference range among the measurement values. Based on the incidental information, the processing circuitry 37 identifies a region corresponding to the identified measurement value and identifies a region adjacent to the region corresponding to the identified measurement value. The processing circuitry 37 generates a composite image by merging images showing the analysis results corresponding to the identified regions (hereinafter referred to as identified regions). The processing circuitry 37 displays the composite image on the display 15.

In the case where, for example, the measurement item corresponding to the measurement value outside the reference range is a valve area of an aortic valve, and the valve area is outside the reference range, the processing circuitry 37 realizing the image processing function 371 identifies the aortic valve among the regions based on the incidental information. The processing circuitry 37 then identifies the left ventricle and the left atrium as regions adjacent to the aortic valve. The processing circuitry 37 generates a composite image by merging an image showing the analysis result of the aortic valve, an image showing the analysis result of the left ventricle, and an image showing the analysis result of the left atrium. The processing circuitry 37 displays the composite image on the display 15. In the present modification, in the case where the measurement value outside the reference range is identified before the processing of step Sb1, medical data regarding the identified regions may be unified to acquire the unified analysis result as in the fifth modification.

According to the configurations mentioned above, the following effects may be obtained.

According to the ultrasound diagnostic apparatus 1 and the medical processing apparatus 20 of the present modification, by including a plurality of measurement values measured at regions in the incidental information, a region corresponding to a measurement value outside a reference range among the measurement values and a region adjacent to the region corresponding to the measurement value outside the reference range can be identified based on the incidental information, and images showing analysis results corresponding to the identified regions can be merged. Therefore, according to the present modification, the analysis result of a region corresponding to the measurement value outside the reference range and the analysis result of a region adjacent to this region can be merged and displayed on the display 15. Thus, the present modification simplifies diagnosis of the motion analysis with respect to the measurement value of the heart, etc. and improves diagnostic efficiency.

(Ninth Modification)

The difference from the above-mentioned embodiment and modifications is that display positions of medical data of regions of the heart (hereinafter referred to as other medical data) collected by other modalities (an X-ray diagnostic apparatus, an X-ray computer tomography apparatus, a magnetic resonance imaging apparatus, a nuclear medicine diagnostic apparatus, etc.) are determined based on the incidental information, and images of the other medical data are displayed on the display 15 together with the analysis results shown in the present embodiment and the fourth modification, etc. In the following, for simplified explanation, the other medical data will be considered as data of a coronary artery image. The other medical data is not limited to medical data of the coronary artery, and may be any data indicating shape information of other regions of the heart, such as the papillary muscle, the tendinous cord, and impulse conducting system. In addition to or instead of the other medical data, an analysis result of the other data (hereinafter referred to as other analysis result) may be used. An example of the other analysis result is a fractional flow reserve (FFR). The other analysis result is not limited to FFR, and may be any data indicating functional information of the heart, such as myocardial scintigraphy.

The communication interface circuitry 31 receives the coronary artery data from other modalities or an image storage apparatus through a network. The communication interface circuitry 31 may also receive FFR regarding a heart of a subject P from other modalities or an image storage device through a network. An analysis parameter, such as FFR, may be analyzed by the processing circuitry 37 realizing the analysis function 373 by using other medical data such as coronary artery data.

The processing circuitry 37 realizing the addition function 375 sets a patient ID, the kind of coronary artery of the analysis target, an image mode, and an analysis parameter name, etc. The kind of coronary artery is, for example, a coronary artery name, which is set by an operator's input through the input interface circuitry 13, or by tag information regarding the coronary artery data, etc. The processing circuitry 37 includes the set coronary artery information in the incidental information. The coronary artery name is, for example, a right coronary artery (RCA) and a left coronary artery (LCA), etc.

The processing circuitry 37 realizing the display control function 377 determines a display position (section) of the analysis result to be displayed in a display area of the display 15 as a layout based on an anatomical positional relationship between a region corresponding to the coronary artery name in the kind of region in the incidental information and a region regarding the analysis result. Specifically, the display position of the analysis result in the layout corresponds to an anatomical position of the coronary artery. In accordance with the determined layout, the processing circuitry 37 displays a profile image of the coronary artery and the analysis result of the coronary artery, etc. on the display 15 together with the analysis results mentioned in the present embodiment and the fourth modification.

Figure 22:
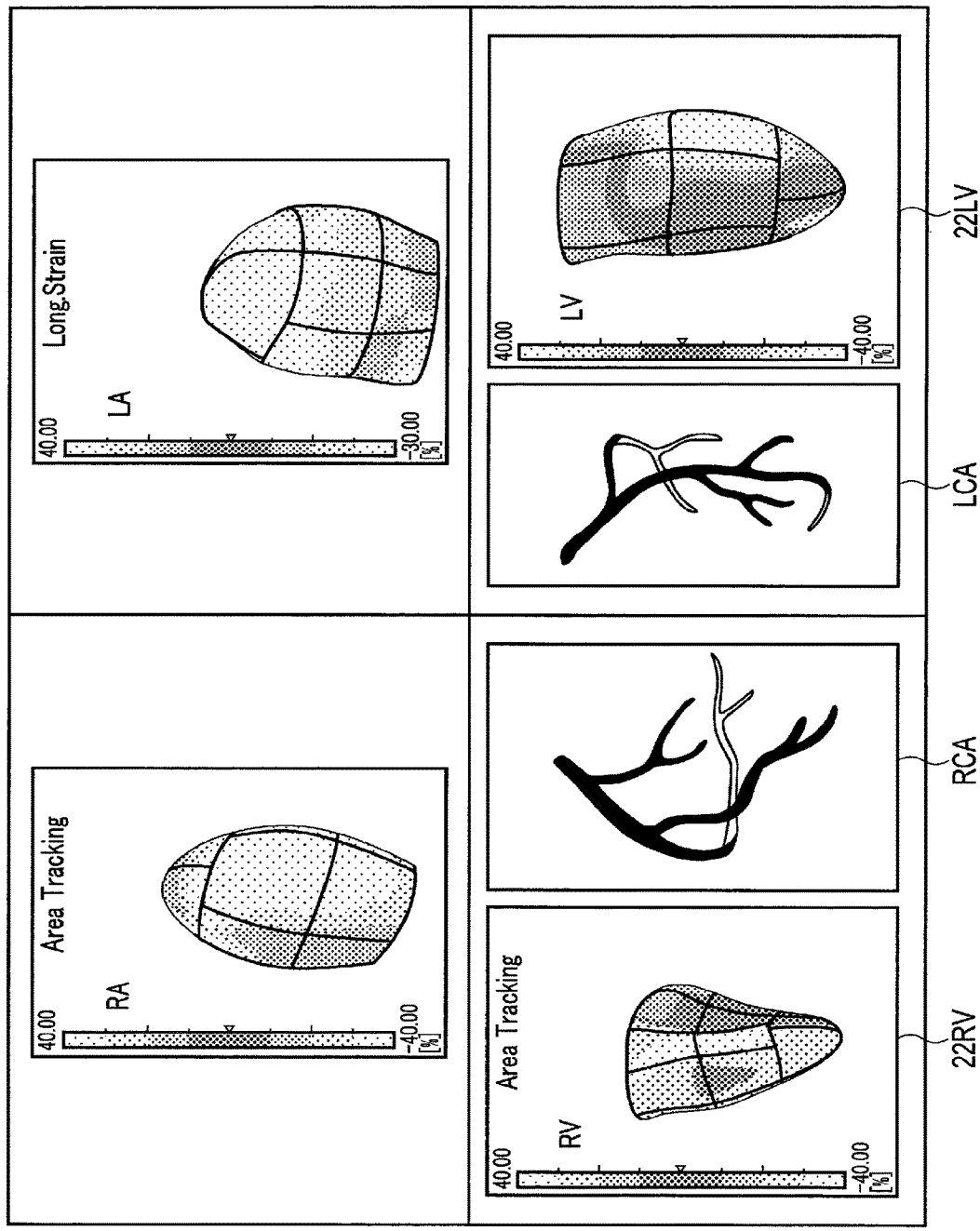
FIG. 22 shows a display example (a tile display) of analysis results of four chambers and coronary artery images (shape information) in a ninth modification of the present embodiment.

FIG. 22 shows a display example (tile display) of the analysis results of four chambers and the coronary artery images (shape information) in the case where the analysis targets are four heart chambers, and the image mode is a surface rendering image. RCA shown in FIG. 22 is an image of the right coronary artery. LCA shown in FIG. 22 is an image of the left coronary artery. The image of the right coronary artery and the image of the left coronary artery are displayed in sync with the heart time phase of the analysis result RA of the right atrium, the analysis result 22RV of the right ventricle, the analysis result LA of the left atrium, and the analysis result of the left ventricle 22LV by the processing circuitry 37 realizing the display control function 377. Instead of the right coronary artery image RCA, a surface rendering image (functional information) of the right coronary artery to which a color phase corresponding to the value of FFR is mapped along the right coronary artery may be used. Instead of the left coronary artery image LCA, a surface rendering image (functional information) of the left coronary artery to which a color phase corresponding to the value of FFR is mapped along the left coronary artery may be used. FIG. 22 shows a layout in which the profile information of the coronary artery is added to the analysis results of the four chambers shown in FIG. 5 in accordance with the anatomical positional relationship between the fourth chambers and the coronary artery.

As an application of the present modification, the processing of the first modification can also be applied to the present modification. In the case where the display example shown in FIG. 22 is, for example, displayed on the display 15, the processing circuitry 37 realizing the image processing function 371 generates, for example, a composite image in response to the operator's instruction.

Figure 23:
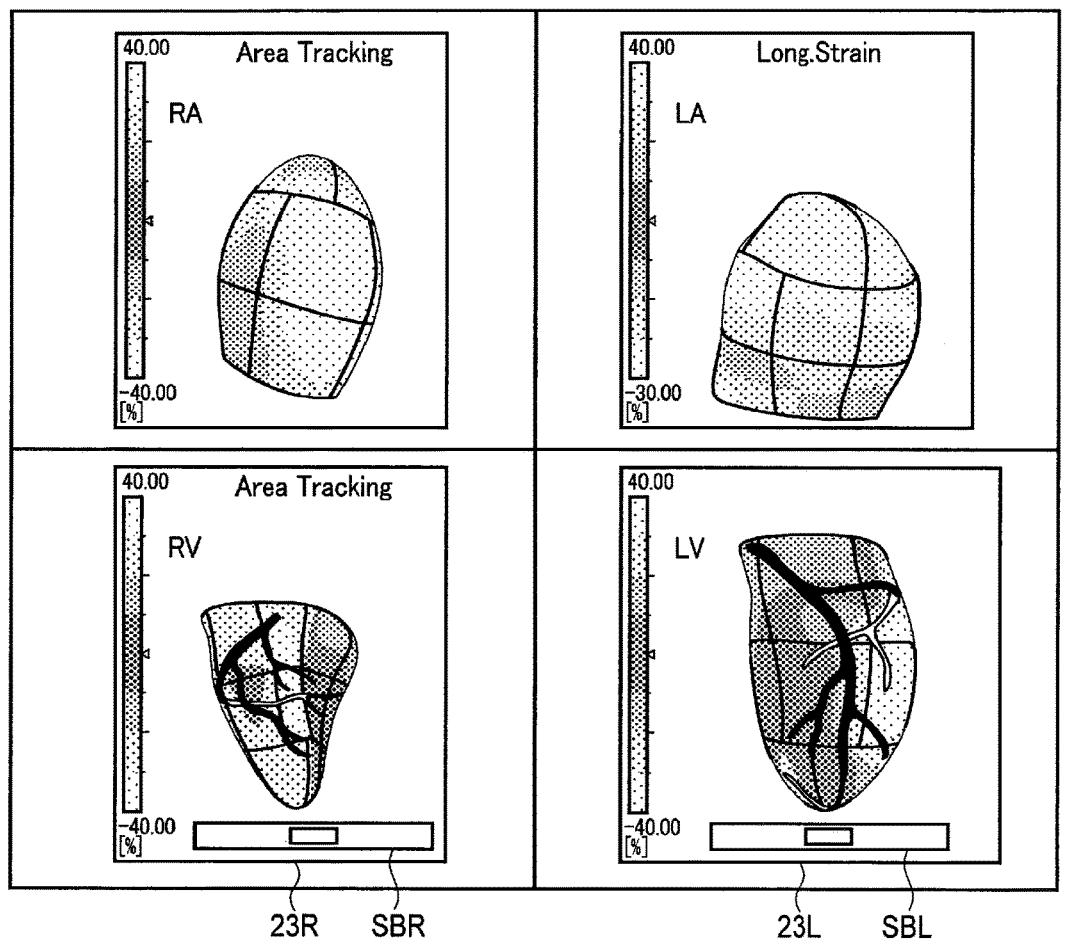
FIG. 23 shows an example of composite images obtained by combining shape information of the coronary artery with the analysis results of the left ventricle and the right ventricle in the ninth modification of the present embodiment.

FIG. 23 shows an example of a composite image obtained by combining shape information of the coronary artery with the analysis results of the left ventricle 22 LV and the right ventricle RV shown in FIG. 22. As shown in FIG. 23, the registration of the analysis result of the left ventricle 23LV and the image of the left coronary artery LCA, and the analysis result of the right ventricle 23RV and the image of the right coronary artery RCA are executed, respectively, in the same heart time phase. A composite image generated for each heart time phase by this registration is displayed on the display 15. Here, the transparency and luminance value, etc. of each of the images of the analysis result of the left ventricle 23LV and the left coronary artery LCA, and the image of the analysis result of the right ventricle 23RV and the right coronary artery RCA, are adjusted by the operator's instruction with respect to scroll bars SBR and SBL provided on each of the lower ends of the composite images 23R and 23L in FIG. 23.

According to the configurations mentioned above, the following effects may be obtained.

According to the ultrasound diagnostic apparatus 1 and the medical processing apparatus 20 of the present modification, display positions of other medical data of the heart collected by other modalities are determined based on the incidental information, and images of the other medical data can be displayed on the display 15, together with the analysis results shown in the present embodiment and the fourth modification, etc. According to the present modification, the composite image with the four valves combined can be displayed in the transparency and luminance value desired by the operator.

As explained above, according to the present modification, by the uniform processing using the incidental information added to the analysis result, that is, the processing related to the function of uniformly displaying the analysis result, the analysis results of the regions in the heart is displayed together with the shape information or the functional information of other regions by a simplified operation, while maintaining the anatomical positional relationship. Thus, by adding the shape information or the functional information of the other regions into consideration, the present modification simplifies, for example, the diagnosis of the local wall motion analysis of the heart chamber, and improves diagnostic efficiency.

Furthermore, as a modification of the present embodiment, in the case of realizing the technical idea of the present ultrasound diagnostic apparatus 1 by the medical processing apparatus 20, the processing of step Sa1 in the flowchart shown in FIG. 2 would be "read out medical image from storage circuitry 33 in a time series." The processing of step Sa1 may also be "acquire medical image from ultrasound diagnostic apparatus 1 or medical image storage device in a time series through communication interface circuitry 31." The above-mentioned medical image may also be an image collected by other modalities such as an X-ray computed tomography apparatus or a magnetic resonance imaging apparatus. In addition, the analysis result may also be an analysis result performed by other modalities, etc.

In addition, the image processing function 371, the analysis function 373, the addition function 375, and the display control function 377 may also be realized as a medical processing method by installing a program (medical processing program) that executes these functions in a computer, such as a work station, and expanding the functions in a memory. Here, the medical processing program causes the computer to add the incidental information including information regarding the kind of heart chamber to the analysis result of each of the heart chambers obtained by analyzing a medical image, and to determine the display position of the analysis result based on the incidental information. The program that causes a computer to execute the above method can be stored and distributed on various types of portable storage medium such as a magnetic disc, an optical disc, or a semiconductor memory.

According to the ultrasound diagnostic apparatus 1 and the medical processing apparatus 20 of the embodiment and at least one of the modifications, etc. mentioned above, the analysis results regarding a plurality of regions in the heart can be displayed in a desired layout by a simplified operation.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical processing apparatus comprising processing circuitry configured to
    add incidental information including information regarding each of a plurality of regions in a heart to an analysis result of each of the regions, the analysis result being obtained by analyzing medical data,
    determine a display position of the analysis result of each of the regions based on the incidental information,
    add first incidental information including information that identifies a first region among the regions to a first analysis result corresponding to the first region,
    add second incidental information including information that identifies a second region among the regions to a second analysis result corresponding to the second region,
    display the first analysis result in a first section among a plurality of sections in a screen of a display based on the first incidental information, and
    display the second analysis result in a second section among the sections based on the second incidental information.

2. The medical processing apparatus according to claim 1, wherein the analysis result includes an image showing a contour of an analysis target region, and the processing circuitry is configured to merge the image corresponding to each of the regions based on the incidental information.

3. The medical processing apparatus according to claim 2, wherein the processing circuitry is configured to
    identify a region designated by an operator among the regions, and a region adjacent to the designated region, and
    merge images corresponding to the identified regions.

4. The medical processing apparatus according to claim 2, wherein
    the incidental information includes information of a disease name regarding the region, and
    the processing circuitry is configured to
        identify a region related to the disease name and a region adjacent to the region related to the disease name from the regions based on the incidental information, and
        merge images corresponding to the identified regions.

5. The medical processing apparatus according to claim 2, wherein
    the incidental information includes a plurality of measurement values measured in the region, and the processing circuitry is configured to
identify a region corresponding to a measurement value outside a reference range among the measurement values, and a region adjacent to the region corresponding to the measurement value outside the reference range, and
merge the image corresponding to the identified region.

6. The medical processing apparatus according to claim 1, wherein the regions include the left ventricle, the left atrium, the right ventricle, and the right atrium.

7. The medical processing apparatus according to claim 1, wherein the processing circuitry is configured to
acquire the first analysis result by analyzing a first time-series image, and
acquire the second analysis result by analyzing a second time-series image that is different from the first time-series image.

8. The medical processing apparatus according to claim 1, wherein the processing circuitry is configured to acquire the first analysis result and the second analysis result by analyzing a common time-series image.

9. The medical processing apparatus according to claim 1, wherein the incidental information includes information regarding a heart time phase.

10. The medical processing apparatus according to claim 9, wherein the processing circuitry is configured to synchronize and display the analysis results of the regions based on the incidental information.

11. The medical processing apparatus according to claim 1, wherein the incidental information includes information regarding a collection date and time of the medical data.

12. The medical processing apparatus according to claim 1, wherein the incidental information includes information regarding progress of treatment to at least one of the regions.

13. The medical processing apparatus according to claim 1, wherein the incidental information includes information regarding an image mode of the analysis result.

14. The medical processing apparatus according to claim 1, wherein
the analysis result is an image showing a contour of the region, a color phase corresponding to a value of an analysis parameter indicating movement of the region being mapped to the image, and
the processing circuitry is configured to generate a composite image by merging the mapped image based on an anatomical positional relationship of the regions.

15. The medical processing apparatus according to claim 1, wherein the processing circuitry is configured to determine the display position within a display area of a screen.

16. The medical processing apparatus according to claim 1, wherein the regions include at least one of a tricuspid valve, a pulmonary valve, a mitral valve, an aortic valve, and a coronary artery.

17. A medical processing apparatus comprising processing circuitry configured to
add incidental information including information regarding each of a plurality of regions in a heart to an analysis result of each of the regions, the analysis result being obtained by analyzing medical data,
determine a display position of the analysis result of each of the regions based on the incidental information, and
acquire a unified analysis result by unifying and analyzing the medical data corresponding to an adjacent region selected by an operator among the regions, wherein
the incidental information includes information unifying the adjacent region as the information of the kind of the regions, and
the processing circuitry is further configured to determine a display position of the unified analysis result based on the information unifying the adjacent region.

18. A medical processing apparatus comprising processing circuitry configured to
add incidental information including information regarding each of a plurality of regions in a heart to an analysis result of each of the regions, the analysis result being obtained by analyzing medical data,
determine a display position of the analysis result of each of the regions based on the incidental information, and wherein
the incidental information includes information of a scanning order with regard to collecting the medical data as the information of the kind of the regions, the scanning order being corresponded to the regions, and
the processing circuitry is further configured to
acquire the analysis result in accordance with the scanning order by analyzing the medical data collected in accordance with the scanning order, and
determine the display position of the analysis result in accordance with an anatomical positional relationship of the regions based on the scanning order in the incidental information.

19. A medical processing apparatus comprising processing circuitry configured to
add incidental information including information regarding a kind concerning each of a plurality of regions in a heart to an analysis result of each of the regions, the analysis result being obtained by analyzing medical data,
determine a display position of the analysis result of each of the regions based on the incidental information, and wherein
the incidental information includes information regarding the collection time and date of the medical data, information regarding a phase of a stress echo, the phase being time that the medical data is collected, information regarding progress of treatment to at least one of the regions, and information regarding an image mode of the analysis result, and
the processing circuitry is further configured to switch between a display position determined based on the kind and the collection date and time, a display position determined based on the kind and the phase, a display position determined based on the kind and the progress, and a display position determined based on the kind and the image mode.

20. A medical processing apparatus comprising processing circuitry configured to
add incidental information including information regarding each of a plurality of regions in a heart to an analysis result of each of the regions, the analysis result being obtained by analyzing medical data,
determine a display position of the analysis result of each of the regions based on the incidental information, and
determine the display position within a display area of each of a plurality of screens.

21. A medical processing method, comprising:
adding incidental information including information regarding each of a plurality of regions in a heart to an analysis result of each of the regions, the analysis result being obtained by analyzing medical data, and
determining a display position of the analysis result of each of the regions based on the incidental information, adding first incidental information including information that identifies a first region among the regions to a first analysis result corresponding to the first region, adding second incidental information including information that identifies a second region among the regions to a second analysis result corresponding to the second region, displaying the first analysis result in a first section among a plurality of sections in a screen of a display based on the first incidental information, and displaying the second analysis result in a second section among the sections based on the second incidental information.

\* \* \* \* \*